US008468001B2

(12) United States Patent (10) Patent No.: US 8,468,001 B2
Ghosh et al. (45) Date of Patent: Jun. 18, 2013

(54) LIGAND IDENTIFICATION AND MATCHING SOFTWARE TOOLS

(75) Inventors: Anirban Ghosh, West Chester, PA (US); Nagasuma Chandra, Bangalore (IN)

(73) Assignees: Infosys Limited, Bangalore (IN); Indian Institute of Science, Bangalore (IN)

( * ) Notice: Subject to any disclaimer, the term of this patent is extended or adjusted under 35 U.S.C. 154(b) by 1215 days.

(21) Appl. No.: 11/869,672

(22) Filed: Oct. 9, 2007

(65) Prior Publication Data

US 2008/0234135 A1 Sep. 25, 2008

Related U.S. Application Data

(60) Provisional application No. 60/896,459, filed on Mar. 22, 2007.

(51) Int. Cl.
*G06G 7/58* (2006.01)
(52) U.S. Cl.
USPC .......................................................... 703/11
(58) Field of Classification Search
USPC .......................................................... 703/11
See application file for complete search history.

(56) References Cited

U.S. PATENT DOCUMENTS

| | | |
|---|---|---|
| 6,694,267 B2 | 2/2004 | Kalghatgi |
| 2002/0115106 A1 | 8/2002 | Shipps et al. |
| 2002/0164617 A1 | 11/2002 | Felsch et al. |
| 2002/0192707 A1 | 12/2002 | Stockman et al. |
| 2004/0086948 A1 | 5/2004 | Stockman et al. |
| 2004/0107054 A1 | 6/2004 | Labute |
| 2004/0117125 A1 | 6/2004 | Chen et al. |
| 2007/0020642 A1 | 1/2007 | Deng et al. |
| 2008/0234996 A1 | 9/2008 | Ghosh et al. |

OTHER PUBLICATIONS

Bacha et al., "Clustering Methods and Their Uses," Daylight Chemical Information Systems, Inc., Santa Fe, NM, Oct. 2007, pp. 1-17.
Branson et al., "The Role of Virtual Screening in Computer Aided Structure-Based Drug Design," *Australian Journal of Chemistry*, Jun.-Aug. 2004, pp. 1029-1037.
Cornell et al., "A Second Generation Force Field for the Simulation of Proteins, Nucleic Acids, and Organic Molecules," *Journal of American Chemistry Society*, 1995, vol. 117, pp. 5179-5197.
*Daylight Theory Manual*, Daylight Chemical Information Systems, Inc., May 9, 2007, 59 pages.
Ghosh, "Chemistry Workbench—A Composite Services Approach to Transform Drug Research," *SETLabs Briefings*, Apr.-Jun. 2007, vol. 5, No. 2, pp. 59-68.
"High Throughput Screening for Small Molecules Binding to Target Active Site," Infosys, retrieved Feb. 9, 2005, 2 pages.
"Homology Modeling," retrieved Mar. 27, 2007, 9 pages. http://en.wikipedia.org/wiki/Homology_modeling.
Karney et al., "Using Binding Free Energy to Guide Ligand Design," Sarnoff Corp., Princeton, NJ, Nov. 2005, pp. 1-11.
Kuntz, "University of New Mexico Biocomputing Workshop," Apr. 22, 2005, 28 pages.
"Life Sciences: Case Studies," Infosys, retrieved Aug. 31, 2005, 2 pages.
O'Donnell et al., "A General Approach for Atom-Type Assignment and the Interconversion of Molecular Structure Files," *Journal of Computational Chemistry*, 1991, vol. 12, No. 2, pp. 209-214.
Regis, *The Info Mesa: Science, Business, and New Age Alchemy on the Santa Fe Plateau*, W. W. Norton & Company, New York, 2003, pp. 13-20, 75-109, 113-130, 162-164, 181-184, 213-219.
Schuffenhauer et al., "An Ontology for Pharmaceutical Ligands and Its Application for in Silico Screening and Library Design," *Journal of Chemical Information and Computer Sciences*, Jul.-Aug. 2002, vol. 42, No. 4, pp. 947-955.
Singh et al., "Molecular Drug Targets and Structure Based Drug Design: A Holistic Approach," *Bioinformation 2006*, Biomedical Informatics Publishing Group, Dec. 23, 2006, vol. 1, No. 8, pp. 314-320.
"Virtual Predictive Tool Rationalizes Lead Compound Identification for New Drug Discovery," Infosys, retrieved Mar. 5, 2007, 2 pages.

*Primary Examiner* — Jerry Lin
(74) *Attorney, Agent, or Firm* — Klarquist Sparkman, LLP

(57) ABSTRACT

Using annotated structural descriptions and binding data for two, four or more input ligand molecules known to bind to a given protein target, a profile of the ligand molecules can be created by identifying patches of ligand molecules which have similar chemical and/or stereochemical descriptions, scored with the use of a weight dataset (e.g., substitution matrix). A database containing annotated molecular descriptions can be searched according to the profile to identify, for example, additional ligands that can bind to the protein target. Information such as the input ligands, the additional ligands, and literature related to these molecules, and modeling tools can be displayed in a user interface.

26 Claims, 26 Drawing Sheets

FIG. 13
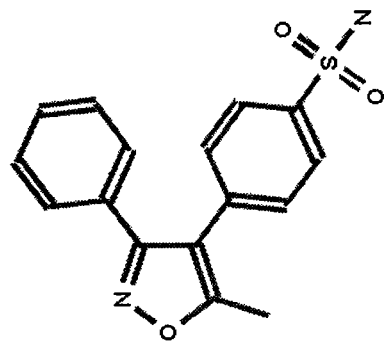
Valdecoxib
Score: 7.5
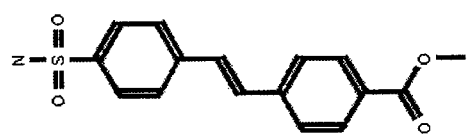
4-[2-(sulphamoyl phenyl) vinyl]
benzoic acid methyl ester
Score: 7.5
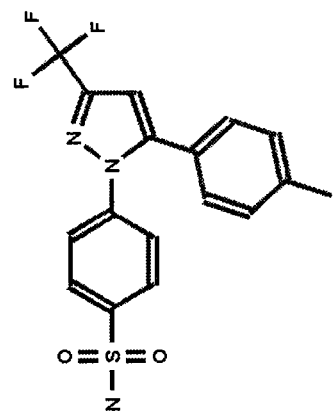
Celecoxib
Score: 15

FIG. 14
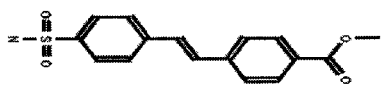
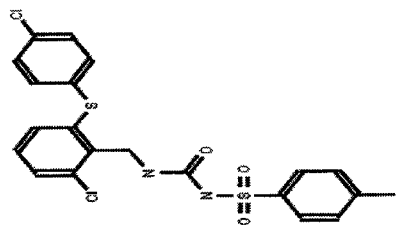
4-[2-(4-sulfamoylphenyl)vinyl]
benzoic acid methyl ester
Score = 17.5
{[({2-chloro-6-[(4-chlorophenyl)
sulfanyl]benzyl}amino)carbonyl]amino}(4-
methylphenyl)dioxo-lambda~6~-sulfane
Score = 10
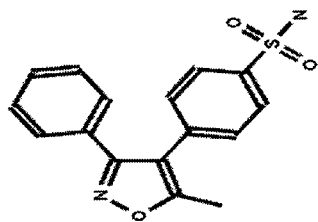
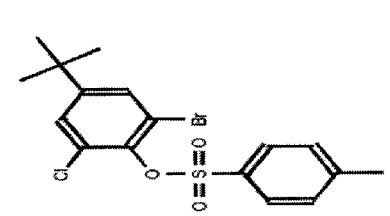
Valdecoxib
Score = 20
2-bromo-4-(tert-butyl)-6-
chlorophen yl4-methylbenzene-
1-sulfonate
Score = 15
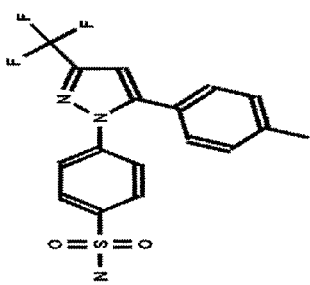
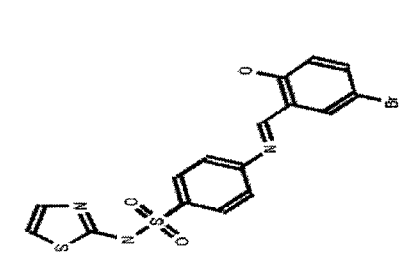
Celecoxib
Score = 22.5
N1-(1,3-thiazol-2-yl)-4-[(5-
bromo-2 -hydroxybenzylidene)
amino]benzene- 1-sulfonamide
Score = 15

| Input Thymidylate Kinase Inhibitors from Literature | | | | Output Homologues from Maybridge |
|---|---|---|---|---|
| Input No. | Known Inhibitor (IUPAC name) | Chemical Structure | Binding Affinity (Ki µM) | |
| 1 | 3'-Azido-2',3'-dideoxy-thymidine-5'-monophosphate [AZTMP] | | 50 | |
| 2 | 1-(2-Deoxy-5-O-phosphoryl-b-D-erythro-pentofuranosyl)-5-(hydroxymethyl)thymine | | 110 | 1-5 anhydrohexitol |
| 3 | 1-(2-deoxy-5-O-phosphoryl-b-D-erythro-pentofuranosyl)-5-(benzyloxymethyl)thymine | | 280 | |
| 4 | 1-(2-Deoxy-5-O-phosphoryl-a-D-erythro-pentofuranosyl)-5-(hydroxymethyl)thymine | | 450 | {5-(5-methyl-2,4-dioxo-1,2,3,4-tetrahydropyrimidin-1-yl)-3-[(methylsulfonyl)oxy]tetrahydrofuran-2-yl}methylpivalate |
| 5 | (Adenosine-5')-P5-(thymidine-5')-pentaphosphate [Ap5T] | | 30 | |
| 6 | 1-5 anhydrohexitol | | 150 | {5-(5-methyl-2,4-dioxo-1,2,3,4-tetrahydropyrimidin-1-yl)-3-[(methylsulfonyl)oxy]tetrahydrofuran-2-yl} methylmethanesulfonate |
| 7 | Thymidine | | 280 | |
| 8 | (E)-5-(2-bromovinyl)-2'-deoxyuridine[BVDU] | | 900 | {3-hydroxy-5-[5-methyl-2,4-dioxo-3, 4-dihydropyrimidin-1(2H)-yl]tetrahydrofuran-2-yl}methyl2,4,6-triisopropylbenzenesulfonate |

FIG. 15

| Selected Inhibitor | Input Data | Output Homologues |
|---|---|---|
| Aspirin 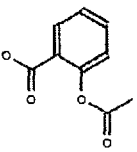 | 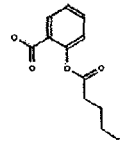 2-acetyloxybenzoic acid | 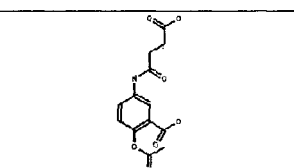 2-pentanoyloxybenzoicacid |
| | 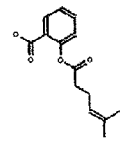 2-acetyloxy-5-(3-carboxypropanoylamino) benzoic acid | 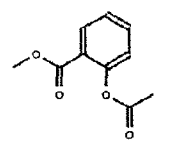 2-(5-methylhex-4-enoyloxy)benzoic acid |
| | 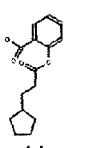 methyl 2-acetyloxybenzoate | 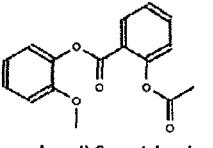 2-(3-cyclopentylpropanoyloxy) benzoic acid |
| | 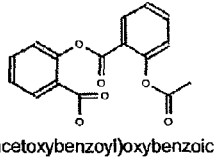 (2-methoxyphenyl) 2-acetyloxybenzoate | 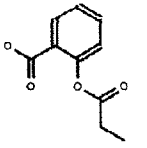 2-(2-acetoxybenzoyl)oxybenzoic acid |
| | 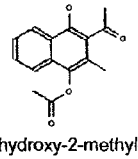 2-propanoyloxybenzoic acid | 3-acetyl-4-hydroxy-2-methyl-1-naphthyl acetate |

FIG. 16

| Selected Inhibitor | Input Data | Output Homologues |
|---|---|---|
| Rofecoxib 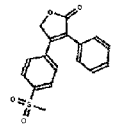 | 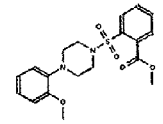 4-(4-methylsulfonylphenyl)-3-phenyl-5H-furan-2-one | 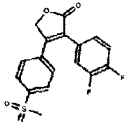 methyl2-{[4-(2-methoxyphenyl)piperazino]sulfonyl}benzoate |
| | 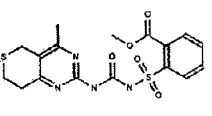 3-(3,4-difluorophenyl)-4-(4-methylsulfonylphenyl)-5H-furan-2-one | 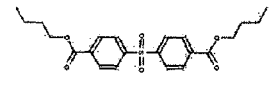 methyl2-[({[(4-methyl-7,8-dihydro-5 H-thiopyrano [4,3-d]pyrimidin-2-yl)amino]carbonyl}amino) sulfonyl]benzoate |
| | 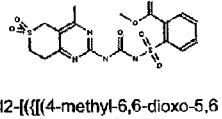 methyl 4-(4-methoxycarbonylphenyl) sulfonyl benzoate | 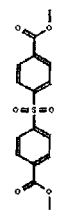 methyl2-[({[(4-methyl-6,6-dioxo-5,6,7,8-tetrahydro-6lambda~6~-thiopyr ano[4,3-d]pyrimidin-2-yl)amino]carbonyl}amino)sulfonyl]benzoate |
| | 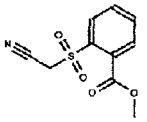 ethyl 4-methylsulfonylbenzoate | methyl2-(cyanomethyl)sulfonyl]benzoate |
| | | 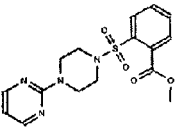 methyl2-[(4-pyrimidin-2-ylpiperazino)sulfonyl] benzoate |

FIG. 17

Ligand Identification: Results

| Ligands | Score |
|---|---|
| OC(COc1ccc(cc1)[N+](O-]=O)cN2COOCC2 | 10 |
| Oc1cc(Cl)cc(Cl)cc1C=Nc2cc(ccc(ccc2N3COOCC3)C(F)(F)F | 10 |
| Oc1c(C1)cc(C1)cc1C=Nc2ccc(cc2)N3COCOC3 | 10 |
| [O-][N+](=O)c1ccc(cc1N2COOCC2)C(F)(F)F | 10 |
| [O-][N+](=O)c1ccc(cc1)N2COCN(CC2)C(=O)N3CCOCC3 | 10 |

The number of relevant matches are 5.

LIGAND IDENTIFICATION AND MATCHING SOFTWARE TOOLS

CROSS REFERENCE TO RELATED APPLICATION

This application claims the benefit of U.S. Provisional Patent Application No. 60/896,459, filed Mar. 22, 2007, titled "LIGAND IDENTIFICATION AND MATCHING SOFTWARE TOOL," which is incorporated herein by reference.

FIELD

The disclosed technologies relate to electronically identifying chemical compounds using one or more software tools.

BACKGROUND

One of the main goals in drug discovery is to identify and develop new ligands with high binding affinity towards a protein target. In some cases the structure of the protein target is known, but in other cases the structure is unknown. A mix of experimental methods and in silico methods is often used for lead identification, and these often make use of automated high-throughput screening (HTS) techniques and combinatorial chemistry. Random screening can be performed using large, diverse libraries, and this can result in identifying a number of lead compounds. However, far more compounds exist (or can be synthesized by combinatorial methods) than can be reasonably evaluated by HTS. Additionally, a number of these lead compounds may fail in the clinical trials phase. Generally, these processes are expensive and time-consuming.

SUMMARY

Using annotated structural descriptions of ligand molecules and binding data for two or more input ligand molecules known to bind to a given protein target, a profile of the ligand molecules can be created which identifies one or more common patches in the ligand molecules. A database containing annotated molecular descriptions can be searched according to the profile to identify additional ligands that may bind to the protein target. Information such as the input ligands, the additional ligands, toxicologic characteristics, and literature related to these molecules can be displayed in a user interface. Techniques described herein do not necessarily require knowledge of the target's structure.

In some embodiments, a method of identifying one or more chemical compounds comprises: generating, from structural descriptions of a set of input chemical compounds and from binding affinity data for the set of input chemical compounds relative to a target protein, a profile describing one or more patches in the set of input chemical compounds; selecting a set of one or more output chemical compounds from a database based at least in part on the profile, wherein the database comprises structural descriptions of a plurality of molecules, the descriptions comprising force field information for one or more atoms described in the descriptions; and storing structural descriptions of members of the set of one or more output chemical compounds in one or more computer-readable media. Generating the profile can comprise performing one or pairwise more sequence alignments of structural descriptions of the input chemical compounds and identifying one or more patches in the input chemical compounds based on the sequence alignments. Generating a profile can further comprise assigning a score to an identified patch. The assigned score can be based at least in part on the number of input chemical compounds in which the identified patch occurs. Performing one or more sequence alignments of structural descriptions of the input chemical compounds can comprise: performing a first set of sequence alignments among a first subset of the input chemical compounds; and performing a second set of sequence alignments among a second subset of the input chemical compounds, wherein the first and second subsets contain no common input chemical compounds. Performing one or more sequence alignments of structural descriptions of the input chemical compounds further comprises performing a third set of sequence alignments among a third subset of the input chemical compounds, the third set comprising chemical compounds from the first and second subsets. Selecting a set of one or more output chemical compounds from a database can comprise assigning scores to one or more chemical compounds in the database based on patches in the one or more chemical compounds, the patches being identified in the profile. Additionally, in some embodiments the second set of one or more compounds can be ordered based on scores assigned to patches in the compounds of the second set. In further embodiments the method can further comprise converting the structural descriptions of a first set of one or more chemical compounds from a first format to a second format.

In some embodiments, a computer-implemented method for identifying one or more chemical compounds comprises: presenting a first user interface configured to receive structural descriptions of a set of input chemical compounds and binding affinity data for the set of input chemical compounds relative to a protein target; receiving the structural descriptions and binding affinity data via the first user interface; providing the structural descriptions and binding affinity data to a computer configured to perform a method described above; receiving a list of output chemical compounds from the computer; displaying a second user interface; and displaying the list of output chemical compounds in a second user interface. In further embodiments, the method comprises displaying a third user interface configured to provide information about at least one of the set of input chemical compounds or at least one of the set of output chemical compounds. In some embodiments, the method further comprises displaying a third user interface configured to receive user inputs for generating a weighting matrix for use by the computer, e.g., for execution of a pairwise similarity search for patch and/or profile generation. In additional embodiments, a third user interface can be displayed and configured to receive a graphical description of one or more chemical compounds.

In some embodiments, a method of generating a description of two or more ligands comprises: receiving structural descriptions of a set of input ligands and binding affinity data for the ligands relative to a protein target; determining, from the structural descriptions and the binding affinity data, a profile describing one or more patches in the set of input ligands; and storing the profile in one or more computer-readable media. Determining a profile can comprise performing one or more pairwise sequence alignments of structural descriptions of the input ligands and identifying one or more patches in the input ligands based on the sequence alignments. In particular embodiments, determining a profile further comprises assigning a score to at least one of the identified one or more patches based on a length of a structural description describing at least one of the identified one or more patches. Determining a profile can also further comprise assigning a score to at least one of the one or more patches based on a profile describing common factors among a set of ligands having a given binding affinity for the protein target.

Determining a profile can also further comprise assigning a score to at least one of the one or more patches based on a weight matrix, wherein the weight matrix describes a probability that given position in a ligand structure is occupied by a given atom. A profile generated according to one or more of the foregoing methods can be stored in one or more computer-readable media.

Additional embodiments include a system for screening chemical compounds, the system comprising: a database comprising descriptions of a plurality of chemical compounds for screening; an input component for receiving descriptions of one or more input chemical compounds, the one or more compounds comprising one or more patches; and a chemical identifier component configured to identify one or more output chemical compounds from the database based the one or more patches of the one or more compounds.

A further embodiment includes a user interface comprising: a first graphical user interface (GUI) component configured to receive descriptions of a set of input molecules and values indicating affinities of members of the set of input molecules to bind to a target molecule; and a second GUI component configured to display descriptions of one or more output molecules selected from a database of annotated molecular descriptions, the one or more output molecules having been selected based on the descriptions of the set of input molecules and the values indicating affinities.

In various embodiments, a first portion of any of the methods disclosed herein can be performed on a first computer and a second portion of the method can be performed on a second computer, the first and second computers being connected by a network. One or more computer-readable media can comprise instructions configured to cause a computer to perform any of the methods described herein. Such one or more computer-readable media can be used in systems comprising processors, e.g., as part of a computer-based system.

This summary is not intended to limit the technologies described herein. The foregoing and other features and advantages of the disclosed technologies will become more apparent from the following detailed description, which proceeds with reference to the accompanying figures.

BRIEF DESCRIPTION OF THE DRAWINGS

FIG. 13 depicts compounds identified using technologies described herein.

FIG. 14 depicts compounds identified using technologies described herein.

FIG. 15 depicts input and output compounds related to experimental results using technologies described herein.

FIG. 16 depicts input and output compounds related to experimental results using technologies described herein.

FIG. 17 depicts input and output compounds related to experimental results using technologies described herein.

FIG. 19 is a diagram of an exemplary embodiment of a user interface.

FIG. 22 is a diagram of an exemplary embodiment of a user interface.

DETAILED DESCRIPTION

General Considerations

Figure 1:
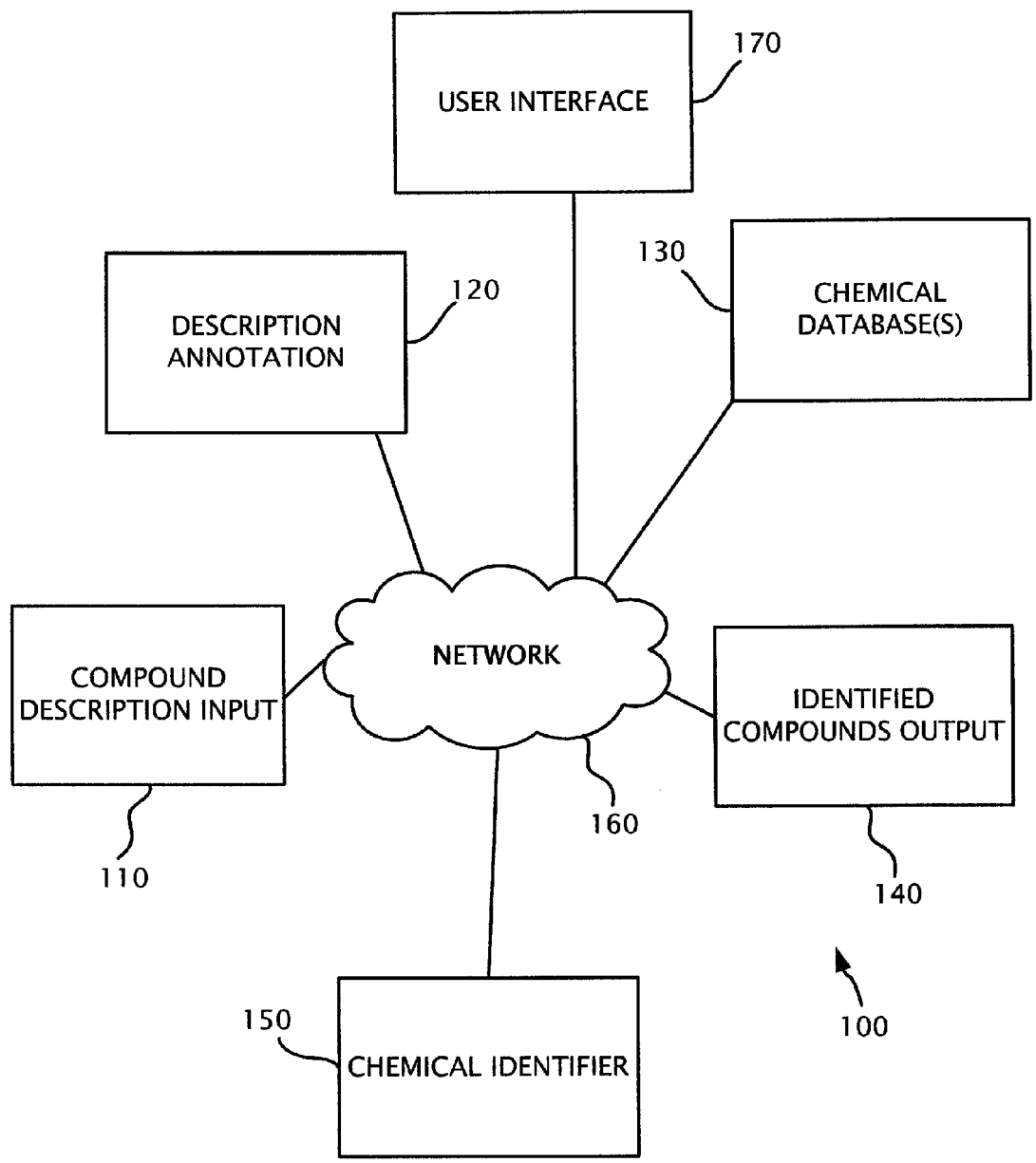
FIG. 1 is a block diagram of an exemplary embodiment of a system for screening chemical compounds.

Disclosed below are representative embodiments of chemical screening techniques and associated apparatus that should not be construed as limiting in any way. Instead, the present disclosure is directed toward all novel and nonobvious features and aspects of the various disclosed methods, apparatus, and equivalents thereof, alone and in various combinations and subcombinations with one another. The disclosed technology is not limited to any specific aspect or feature, or combination thereof, nor do the disclosed methods and apparatus require that any one or more specific advantages be present or problems be solved.

As used in this application and in the claims, the singular forms "a," "an" and "the" include the plural forms unless the context clearly dictates otherwise. Additionally, the term "includes" means "comprises." The phrase "and/or" can mean "and," "or," "both," or "two or more of."

Although the operations of some of the disclosed methods and apparatus are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods and apparatus can be used in conjunction with other methods and apparatus. Additionally, the description sometimes uses terms like "determine" and "select" to describe the disclosed methods. These terms are high-level abstractions of the actual operations that are performed. The actual operations that correspond to these terms will vary depending on the particular implementation and are readily discernible by one of ordinary skill in the art. The disclosed embodiments can be implemented in, for example, a wide variety of integrated circuits, computer systems, and/or software configurations.

Any of the methods described herein can be performed or simulated (at least in part) using software comprising computer-executable instructions stored on one or more computer-readable media (e.g., communication media, storage media, tangible media, or the like). Furthermore, any intermediate or final results of the disclosed methods can be stored on one or more computer-readable media. Any such software can be executed on a single computer, on a networked computer (for example, via the Internet, a wide-area network, a local-area network, a client-server network, or other such network), a set of computers, a grid, or the like. For clarity, only certain selected aspects of the software-based implementations are described. At least some other details that are well known in the art are omitted. For the same reason, computer hardware is not described in further detail. It should be understood that the disclosed technology is not limited to any specific computer language, program, or computer. For instance, a wide variety of commercially available computer languages, programs, and computers can be used.

Generally, as used herein, a "structural description" of a chemical compound refers to a description of relationships of atoms in a molecule. A structural description can include properties such as: numbers and types of atoms; arrangements of atoms; bonds between atoms; bond angles and/or torsion angles for connected atoms; and fragment types.

Generally, as used herein, a "patch" refers to a portion of a ligand molecule that can bind to a portion of another molecule, for example, a protein. The portion to which a patch binds is referred to herein as a "target" or "protein target active site," and the molecule containing the target active site is sometimes called a "protein target molecule."

As generally used herein, "a force field" refers to functional form and parameter sets used to describe the potential energy of a system of particles (e.g., atoms).

As generally used herein, an "annotated description" of a chemical compound refers to a first structural description that has been created from a second structural description, the second structural description having been modified to include additional chemical and/or stereochemical information about the compound. The additional information can include, for example, chemical bond information (e.g., atomic size, hybridization, charge on an atom, type of bonding), hybridization information, and force field information. At least some of the additional information can be expressed in a portion of the first structural description called an "atom type label."

System Overview

FIG. 1 shows a block diagram of one embodiment of a system 100 that can be used to screen chemical compounds. The depicted embodiment comprises a compound description input component 110 configured to receive descriptions of one or more chemical compounds. In some embodiments, the system 100 can further comprise a description annotation component 120 configured to modify the received descriptions by, for example, including additional parameters that affect binding. The additional parameters can be obtained at least in part from one or more chemical databases 130. In some embodiments the databases 130 can also provide information to a chemical identifier component 150, which is configured to screen a plurality of compounds to identify a subset of compounds that meet selected criteria (e.g., that bind or likely bind to a selected protein target). The identified compounds can be stored and/or displayed by the identified compounds output component 140. In particular embodiments, one or more of the compound description input component 110 and the identified compounds output component 140 can be used in conjunction with a user interface (UI) component 170. For example, the UI component 170 can be configured to receive input data for the compound description input component 110 and/or display output data from the identified compounds output component 140. In embodiments where two or more of the components of system 100 are implemented on separate computers, the computers can be coupled together by one or more networks, such as network 160.

Exemplary Embodiments of Modifying Structural Descriptions

In some embodiments, a structural description of one or more chemical compounds can be modified to include additional parameters describing properties of the compounds. For example, a description can be modified to include parameters that affect binding, such as atomic-level chemical and conformational parameters. In further embodiments, a one- or two-dimensional structural description is modified to include three-dimensional descriptors.

One example of a specification that can be used for describing the structure of chemical molecules is Simplified Molecular Input Line Entry Specification (SMILES). At least some embodiments described below utilize SMILES. However, further embodiments can also use one or more additional notation specifications, such as Wisswesser Line Notation (WLN), SYBYL Line Notation (SLN), and International Chemical Identifier (InChI). Generally, one-dimensional notation specifications are used with technologies described herein, but in some embodiments two- or three-dimensional notation specifications can be used.

Figure 2:
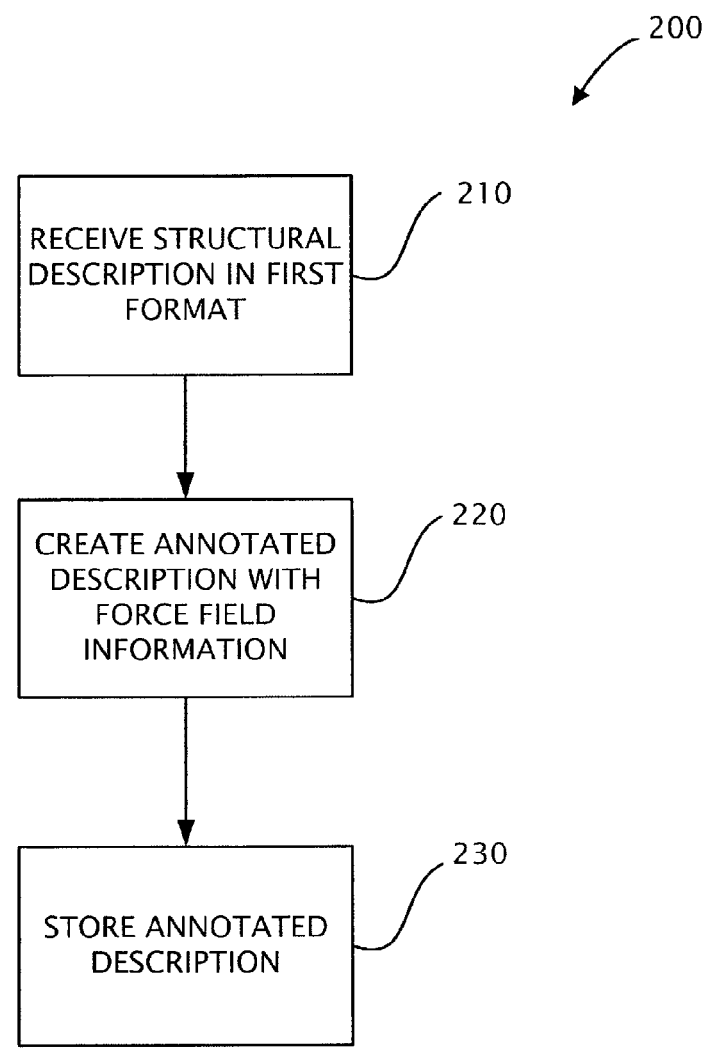
FIG. 2 is a block diagram of one embodiment of a method of modifying a structural description of a chemical compound.

FIG. 2 is a block diagram of one embodiment of a method 200 of modifying a structural description of a chemical compound. In a method act 210, a structural description of a chemical compound is received, for example, via the compound description input component 110. The description can be in one or more formats, such as SMILES. The description is annotated to include force field information for one or more atoms identified in the description (method act 220), and the annotated description is stored in one or more computer-readable media (method act 230). In further embodiments, in a method act 220 the structural description can be translated from a first format to one or more additional formats. The annotated description can then be created at least in part based on the description as expressed in the one or more additional formats.

Figure 3:
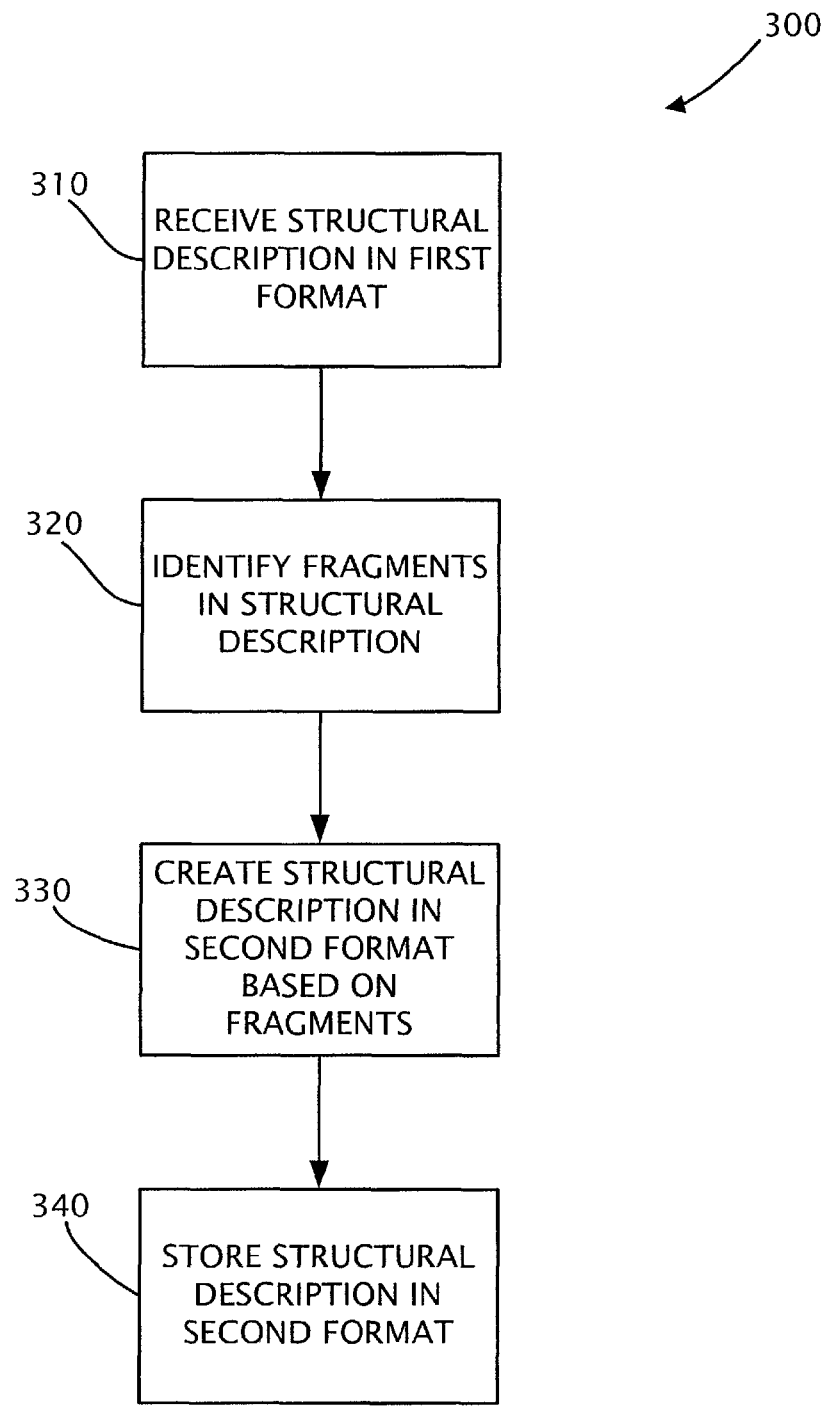
FIG. 3 is a block diagram of another embodiment of a method of modifying a structural description of a chemical compound.

FIG. 3 is a block diagram of an additional embodiment of a method 300 of modifying a structural description of a chemical compound. In a method act 310, a structural description of a chemical compound is received in a first format. The description can be parsed to identify one or more fragments that make up the compound (method act 320). The fragments can be indicative of, for example, short chemical topology linked to the biological activity of the compound. Based on one or more of the fragments, the structural description can be expressed in a second format (method act 330) stored in one or more computer-readable media (method act 340).

Figure 4:
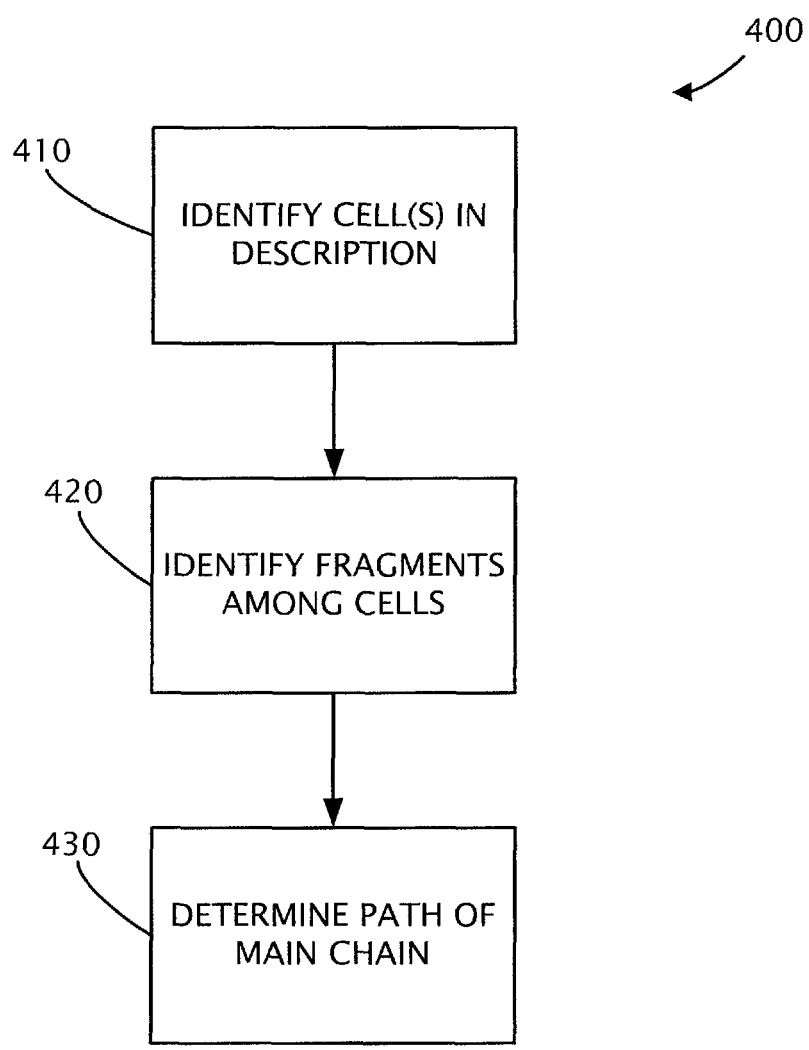
FIG. 4 is a block diagram of one embodiment of an implementation of a portion of the method depicted in FIG. 3.

In some embodiments, the first format can be the SMILES format, while in further embodiments one or more additional formats can be used. FIG. 4 shows a block diagram of one exemplary method 400 that can be used to implement method act 320 of method 300.

In a method act 410, one or more cells are identified in the structural description. A cell can be defined as a basic unit in the SMILES format or other format. In some embodiments, a given cell can be, for example: a single atom (e.g., O, C, [C@], [C@]1, [C@@], [C@@]1, ([H])); a simple group (for example, O(—OH), N(—NH2), Cl(—Cl)); or a fragment (for example, an aliphatic, alicyclic or aromatic group) of the description's main chain or a side chain. In a method act 420 one or more fragments are identified from the identified cells. In a method act 430, one or more side chains of fragments of the main chain are read, and the path for the main chain of the compound is determined.

Returning to FIG. 3, as mentioned above the structural description is created according to one or more fragments (method act 330). In some embodiments, various portions of the description can be written using one or more types of brackets, braces, or parentheses. In some embodiments parts of these portions can be expressed using the SMILES format or another format and delineated using brackets or similar marks. For example, in some embodiments, a side chain of a fragment can be expressed inside the parentheses marks '( )'. A fragment can be expressed inside the braces '{ }'. In further embodiments, a fragment can be associated with a number or other symbol indicating the type of the fragment (e.g., 1 for aliphatic, 2 for alicyclic, 3 for aromatic). This format is sometimes referred to as "Fragmented SMILES" or "FSMILES." A typical FSMILES description can have a format such as: $n_1$ {Fragment 1} $n_2$ {Fragment 2} $n_3$ {Fragment 3} . . . , where $n_i$ identifies the fragment type of a fragment and is equal to 1, 2 or 3. In some embodiments, FSMILES for a given compound is unique, for example, in terms of the main chain length (i.e., the number of fragments) and the actual fragments. Further embodiments distinguish between supported fragment types (e.g., aliphatic, alicyclic, aromatic and unsupported fragment types (e.g., bicyclic).

As further examples, using one or more techniques described herein, the SMILES descriptions shown in Table 1 can be converted to the corresponding FSMILES descriptions shown in Table 2.

TABLE 1

| Description No. | SMILES Description |
|---|---|
| 1 | COCCCNC(=S)NNS(=O)(=O)c1ccc(C)cc1 |
| 2 | CSCC(=N)NS(=O)(=O)c1ccc(Cl)cc1 |
| 3 | CC(C)(C)SCCNS(=O)(=O)c1ccc(Cl)cc1 |
| 4 | CC(C)(C)SCCNS(=O)(=O)c1ccc(Cl)c(Cl)c1 |
| 5 | CN(C)CCCNS(=O)(=O)c1ccc(C)c(F)c1C |
| 6 | CCOC(=O)NS(=O)(=O)c1ccccc1Cl |
| 7 | NNS(=O)(=O)c1ccc(Cl)s1 |

TABLE 1-continued

| Description No. | SMILES Description |
|---|---|
| 8 | NS(=O)(=O)c1ccc(Cl)s1 |
| 9 | NS(=O)(=O)c1ccc(Br)s1 |
| 10 | NS(=O)(=O)c1ccc(Cl)c(Cl)c1 |

At least some embodiments of the FSMILES format can have one or more advantages in comparison to at least some embodiments of the SMILES format. For example, for a SMILES format description: aromatic rings, alicyclic rings, and/or poly rings are not necessarily shown as being contiguous; visualization of the compound based on human examination of the description can be difficult; and alignment of chemical compounds of the same family (e.g., identifying a common moiety) can be difficult due to differences in their respective SMILES format descriptions. However, for a given FSMILES description of the same compound: aromatic rings, alicyclic rings, and/or poly rings are shown as being contiguous; visualization of the compound based on examination of the description can be relatively easy; and alignment of chemical compounds of the same family (e.g., identifying a common moiety) can be relatively simple due to similarities in their respective FSMILES format descriptions.

TABLE 2

| Description No. | FSMILES Description |
|---|---|
| 1 | 1{C}1{O}1{C}1{C}1{C}1{N}1{C(=S)}1{N}1{N}1{S(=O)(=O)}3{c1ccc*cc1}1{C} |
| 2 | 1{C}1{S}1{C}1{C(=N)}1{N}1{S(=O)(=O)}3{c1ccc(Cl)cc1} |
| 3 | 1{C}1{C(C)(C)}1{S}1{C}1{C}1{N}1{S(=O)(=O)}3{c1ccc(Cl)cc1} |
| 4 | 1{C}1{C(C)(C)}1{S}1{C}1{C}1{N}1{S(=O)(=O)}3{c1ccc(Cl)c(Cl)c1} |
| 5 | 1{C}1{N(C)}1{C}1{C}1{C}1{N}1{S(=O)(=O)}3{c1ccc*c(F)c1(C)}1{C} |
| 6 | 1{C}1{C}1{O}1{C(=O)}1{N}1{S(=O)(=O)}3{c1ccccc1(Cl)} |
| 7 | 1{N(N)}1{S(=O)(=O)}3{c1ccc(Cl)s1} |
| 8 | 1{S(N)(=O)(=O)}3{c1ccc(Cl)s1} |
| 9 | 1{S(N)(=O)(=O)}3{c1ccc(Br)s1} |
| 10 | 1{S(N)(=O)(=O)}3{c1ccc(Cl)c(Cl)c1} |

In a further embodiment of the method 300, a description in the FSMILES format can be converted to a format called "SMILES Force Field" or "SMILESFF." The SMILESFF format comprises a structural description of a chemical compound that includes force field parameter information for one or more atoms identified in the description. In some embodiments, the force field information can be obtained, for example, from a database such as the Assisted Model Building and Energy Refinement (AMBER) database. In further embodiments, at least some of the force field information can be supplied by user input or determined experimentally.

Figure 5:
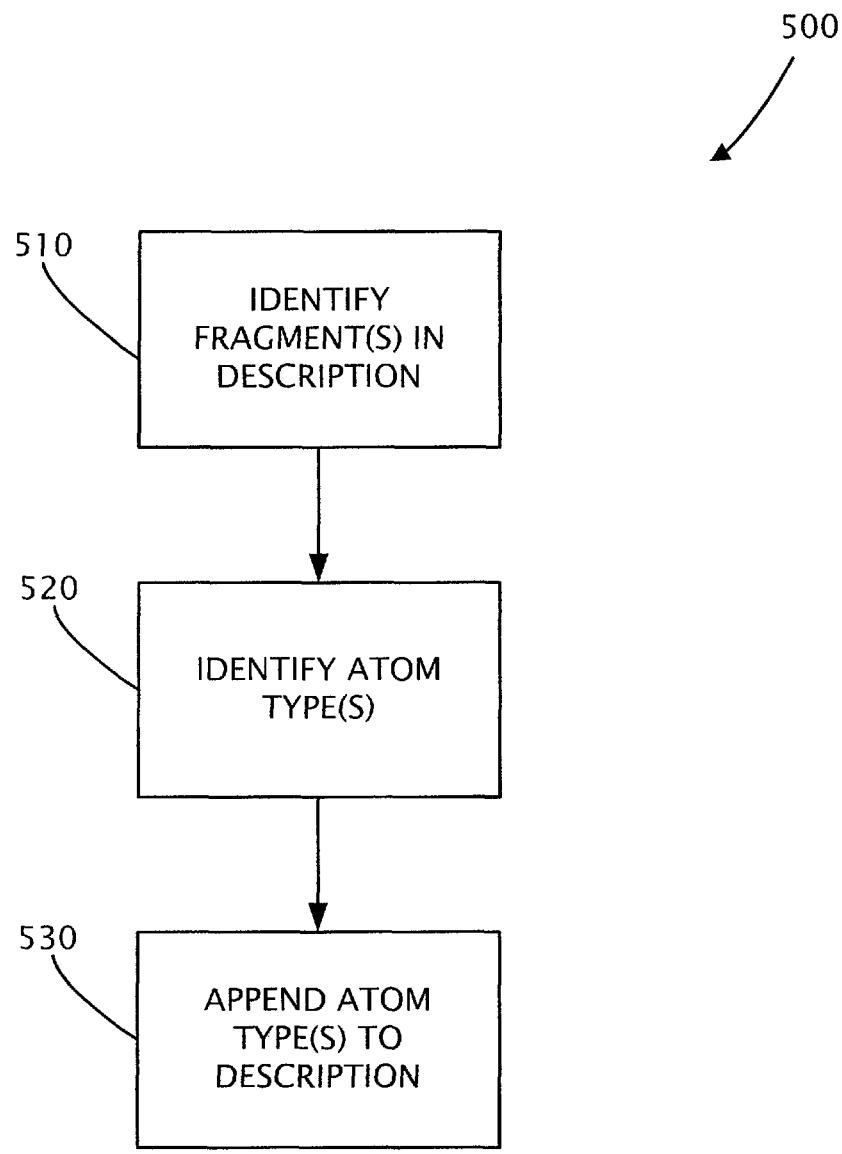
FIG. 5 is a block diagram of an exemplary embodiment of a method for converting a structural chemical description from a first format to a second format.

FIG. 5 shows a block diagram of one embodiment of a method 500 for converting a description from the FSMILES format to the SMILESFF format. In a method act 510, one or more fragments are identified in the description. In a method act 520, one or more atom types are identified which classify atoms in the description fragments according to their respective environments. In some embodiments, the atom types can be based on an AMBER classification, according to, for example, charge, hybridization, ionization and neighborhood environment of the atoms. In further embodiments, one or more additional criteria can be used in determining atom types. Table 4 shows a list of labels for atom types used in some embodiments. For example, an $sp^3$ carbon atom with four explicit substituents can be identified as type "CT," and a sulfur atom in cysteine can be identified as type "SH." In a method act 530, one or more atom types can be appended to the description.

In particular embodiments, at least some of the atom types can be identified using information that identifies the type of a fragment. For example, using the FSMILES format described above ($n_1$ {Fragment 1} $n_2$ {Fragment 2} $n_3$ {Fragment 3} . . . ), $n_i$ can be used to identify atom types in a fragment i. Additionally, cyclic fragments can be classified based on the fragment ring sizes and the presence of any hetero atoms in the rings.

In further examples, using one or more techniques described herein, the FSMILES descriptions shown in Table 2 can be converted to the corresponding SMILESFF descriptions shown in Table 3.

TABLE 3

| Description No. | SMILESFF Description |
|---|---|
| 1 | 1{C<CT>}1{O<OS>}1{C<CT>}1{C<CT>}1{C<CT>}1{N<NT>}1{C<CT>(=S<SD>)}1{N<NT>}1{N<NT>}1{S<SD>(=O<O>)(=O<O>)}3{c<CA>1c<CA>c<CA>c<CA>*c<CA>c<CA>1}1{C<CT>} |
| 2 | 1{C<CT>}1{S<SH>}1{C<CT>}1{C<CT>(=N<ND>)}1{N<NT>}1{S<SD>(=O<O>)(=O<O>)}3{c<CA>1c<CA>c<CA>c<CA>(C<CL>1)c<CA>c<CA>1} |
| 3 | 1{C<CT>}1{C<CT>(C<CT>)(C<CT>)}1{S<SH>}1{C<CT>}1{C<CT>}1{N<NT>}1{S<SD>(=O<O>)(=O<O>)}3{c<CA>1c<CA>c<CA>c<CA>(C<CL>1)c<CA>c<CA>1} |
| 4 | 1{C<CT>}1{C<CT>(C<CT>)(C<CT>)}1{S<SH>}1{C<CT>}1{C<CT>}1{N<NT>}1{S<SD>(=O<O>)(=O<O>)}3{c<CA>1c<CA>c<CA>c<CA>(C<CL>1)c<CA>(C<CL>1)c<CA>1} |
| 5 | 1{C<CT>}1{N<NT>(C<CT>)}1{C<CT>}1{C<CT>}1{C<CT>}1{N<NT>}1{S<SD>(=O<O>)(=O<O>)}3{c<CA>1c<CA>c<CA>c<CA>*c<CA>(F<F>)c<CA>1(C<CT>)}1{C<CT>} |
| 6 | 1{C<CT>}1{C<CT>}1{O<OS>}1{C<C>(=O<O>)}1{N<NT>}1{S<SD>(=O<O>)(=O<O>)}3{c<CA>1c<CA>c<CA>c<CA>c<CA>c<CA>c<CA>1(C<CL>1)} |
| 7 | 1{N<NT>(N<NT>)}1{S<SD>(=O<O>)(=O<O>)}3{c<CS>1c<C*>c<C*>c<CS>(C<CL>1)s<SA>1} |
| 8 | 1{S<SH>(N<NT>)(=O<O>)(=O<O>)}3{c<CS>1c<C*>c<C*>c<CS>(C<CL>1)s<SA>1} |
| 9 | 1{S<SH>(N<NT>)(=O<O>)(=O<O>)}3{c<CS>1c<C*>c<C*>c<CS>(B<BR>r)s<SA>1} |
| 10 | 1{S<SH>(N<NT>)(=O<O>)(=O<O>)}3{c<CA>1c<CA>c<CA>c<CA>(C<CL>1)c<CA>(C<CL>1)c<CA>1} |

In the SMILESFF descriptions shown in Table 3, the atom type for a given fragment appears between the brackets '< >' adjacent the fragment.

In further embodiments, a description in SMILESFF format can be converted to an additional format. For example, the SMILESFF description can be transformed to a description comprising single-letter representations for most or all atom types from the AMBER list in Table 4. One exemplary embodiment of such a format is referred to herein as "SMILES Force Field Transformed" (SMILESFFTR). Table 4, in the column labeled "Single-letter Notation," indicates an exemplary notation for each atom type. In the depicted embodiment, the parentheses brackets '( )' can also be represented using a single-letter notation, as shown in Table 4.

TABLE 4

| Atom Type Label | Description | Single-letter Notation |
|---|---|---|
| C | sp2 carbonyl carbon and aromatic carbon with hydroxyl substituent in tyrosine | a |
| CA | sp2 aromatic carbon in 6-membered ring with 1 substituent | b |
| CB | sp2 aromatic carbon at junction between 5- and 6-membered rings | c |
| CC | sp2 aromatic carbon in 5-membered ring with 1 substituent and next to a nitrogen | d |
| CK | sp$^2$ aromatic carbon in 5-membered ring between 2 nitrogens and bonded to 1 hydrogen (in purine) | e |
| CM | sp2 carbon in pyrimidine at position 5 or 6 | f |
| CN | sp2 aromatic junction carbon in between 5- and 6-membered rings | g |
| | | h |
| CQ | sp2 carbon in 6-membered ring of purine between 2 NC nitrogens and bonded to 1 hydrogen | |
| CR | sp2 aromatic carbon in 5-membered ring between 2 nitrogens and bonded to 1 H (in his) | i |
| CT | sp3 carbon with 4 explicit substituents | j |
| CV | sp2 aromatic carbon in 5-membered ring bonded to 1 N and bonded to an explicit hydrogen | k |
| CW | sp2 aromatic carbon in 5-membered ring bonded to 1 N—H and bonded to an explicit hydrogen | l |
| C* | sp$^2$ aromatic carbon in 5-membered ring with 1 substituent | m |
| CO | sp2 aromatic carbon next to oxygen | n |
| CS | sp2 aromatic carbon next to sulfur | o |
| C! | generic sp2 carbon | p |
| C# | generic sp carbon | q |
| C& | sp carbon as in cyanide | r |
| C\| | sp2 carbon aromatic with one substituent | s |
| N# | Nitrogen connected by a triple bond | t |
| N | sp2 nitrogen in amide group | u |
| NA | sp2 nitrogen in 5-membered ring with hydrogen attached | v |
| NB | sp2 nitrogen in 5-membered ring with lone pairs | w |
| NC | sp2 nitrogen in 6-membered ring with lone pairs | x |
| NT | sp3 nitrogen with 3 substituents | y |
| ND | Nitrogen connected by a double bond | z |
| N2 | sp2 nitrogen in base NH2 group or arginine NH2 | A |

TABLE 4-continued

| Atom Type Label | Description | Single-letter Notation |
|---|---|---|
| N3 | sp3 nitrogen with 4 substituents | B |
| N* | sp2 nitrogen in purine or pyrimidine with alkyl group attached | C |
| O | carbonyl oxygen | D |
| OH | alcohol oxygen | E |
| OS | ether or ester oxygen | F |
| OW | water oxygen | G |
| OA | Aromatic oxygen | H |
| O2 | carboxyl or phosphate nonbonded oxygen | I |
| S | sulfur in disulfide linkage or methionine | J |
| SD | sulfur connected by a double bond | K |
| SA | Aromatic sulfur as in thiophene | L |
| SH | sulfur in cystine | M |
| P | phosphorus in phosphate group | N |
| CO | calcium ion(+II) | O |
| IM | chloride ion | P |
| I | iodide ion | Q |
| F | fluoride ion | R |
| BR | bromide ion | S |
| CU | cupric ion | T |
| MG | magnesium ion | U |
| QC | cesium ion | V |
| QK | potassium ion | W |
| QN | sodium ion | X |
| ( | opening bracket | Y |
| ) | closing bracket | Z |

For example, the SMILESFF descriptions shown in Table 3 can be converted to the SMILESFFTR descriptions shown in Table 5.

In additional embodiments, the techniques described herein can be used to convert a canonical SMILES description to FSMILES, then to SMILESFF, and then to SMILES-FFTR. In further embodiments, descriptions can be converted "back" to another format. For example, a description in SMILESFF format can be converted to an FSMILES format description or a SMILES format description.

TABLE 5

| Description No. | SMILESFFTR Description |
|---|---|
| 1 | jMjjYzZyKYDZYDZbbbbYCLZbb |
| 2 | jMjjYzZyKYDZYDZbbbbYCLZbb |
| 3 | jjYjZYjZMjjyKYDZYDZbbbbYCLZbb |
| 4 | jjYjZYjZMjjyKYDZYDZbbbbYCLZbYCLZb |
| 5 | jyYjZjjjyKYDZYDZbbbbbYRZbYjZj |
| 6 | jjFaYDZyKYDZYDZbbbbbbYCLZ |
| 7 | yYyZKYDZYDZommoYCLZL |
| 8 | MYyZYDZYDZommoYCLZL |
| 9 | MYyZYDZYDZommoYSZL |
| 10 | MYyZYDZYDZbbbbYCLZbYCLZb |

Exemplary Embodiments of Methods for Screening Chemical Compounds

Some screening methods obtain hits based on a Root Mean Squared Deviation (RMSD) value calculated by superimposing a reference molecule on a target molecule. As the RMSD is an average, it looks for a "best fit" where most or all of the atoms for one molecule can be superimposed on most or all of the atoms for the target molecule. However, when two molecular structures are similar in all but one area, this difference can create a relatively large RMSD, which overstates the dissimilarity between the two structures. For example, subtle pendant group variations or minor changes at linker regions can contribute to a higher RMSD value. As an example, if Celecoxib is used as an input molecule in an RMSD-based screening method, it is unlikely that Valdecoxib will appear as a hit, owing to differences in structure between the two molecules. However, Celecoxib and Valdecoxib are both known Cyclooxygenase-2 (Cox-2) inhibitors.

The reliability of intrinsic coordinate positions from poor resolution crystal structures used for calculation of RMSD is at times ambiguous. Also, RMSD calculations can be computationally expensive, since careful analysis is required wherein RMSD is calculated first for all atoms and then again for backbone atoms. In the case of protein superimposition, a "per residue" change is found to have an impact on RMSD calculation, but in the case of small molecules, in the absence of residues, a "per atom" change would have a large impact on RMSD calculation, often rendering 3-D superposition methods for small molecules erroneous and computationally intensive.

Figure 26:
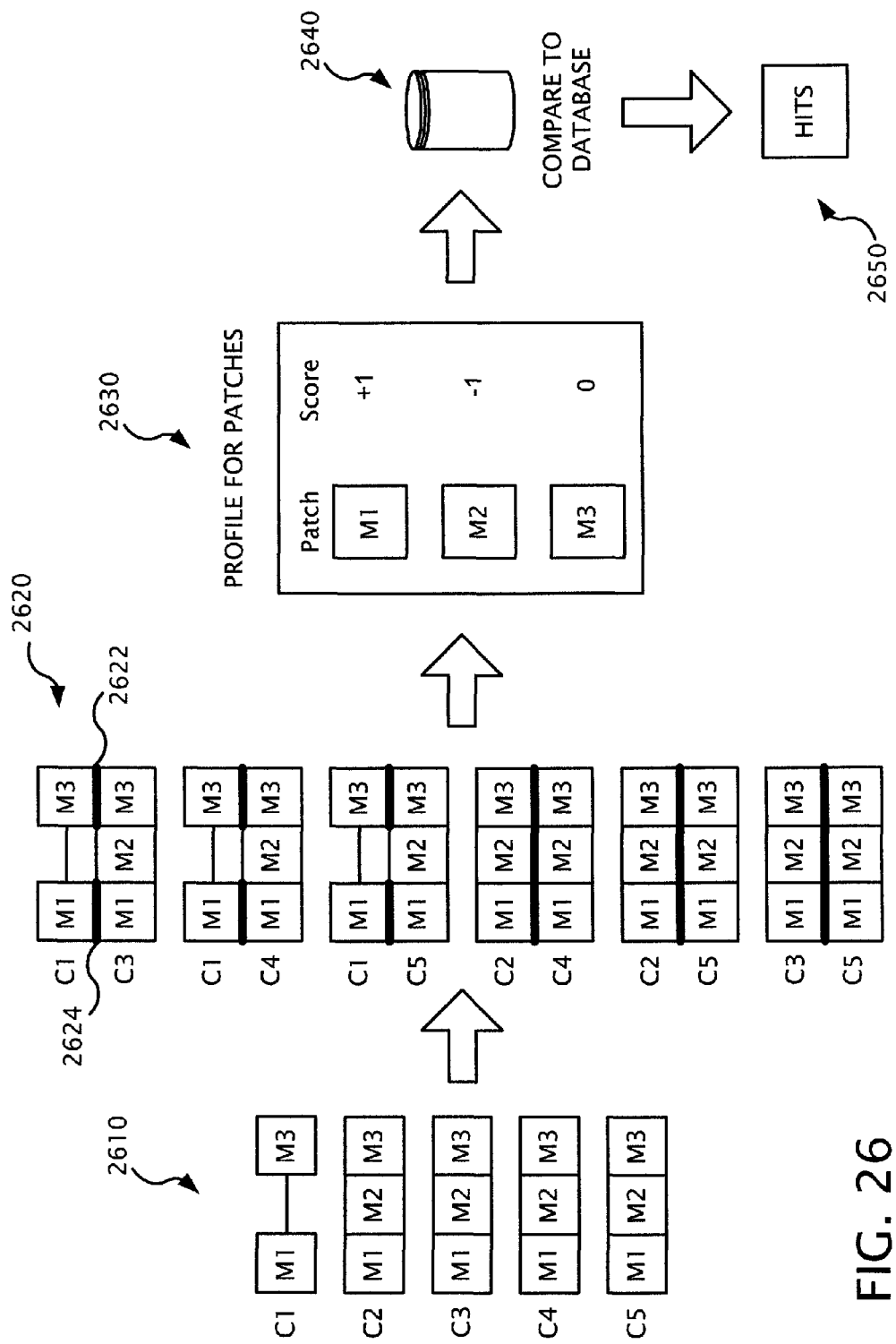
FIG. 26 is an overview of an exemplary embodiment of a method of screening chemical compounds.

FIG. 26 provides an overview of an exemplary embodiment of a method of screening chemical compounds. At 2610 a description of a group of compounds, individually labeled C1 through C5, is received. Each compound comprises one or more patches, which in FIG. 26 are labeled "M1," "M2" or "M3." (Although some compounds, e.g., compounds C4 and C5, have the same patches, this does not necessarily mean that C4 and C5 are chemically identical. The compounds can comprise additional features not shown in FIG. 26.) Using, for example, techniques described below, common patches are identified among the compounds, as shown at 2620. In FIG. 26, lines such as bolded lines 2622, 2624 indicate common patches among compounds. At 2630 a profile for the patches is created with scores describing how the patch affects binding of a compound to a protein target. At 2640 a chemical database is searched to identify additional compounds comprising one or more patches listed in the profile. These search results are used to produce a list of possible hits at 2650. Various aspects of the embodiment of FIG. 26 are described below in more detail.

Figure 6:
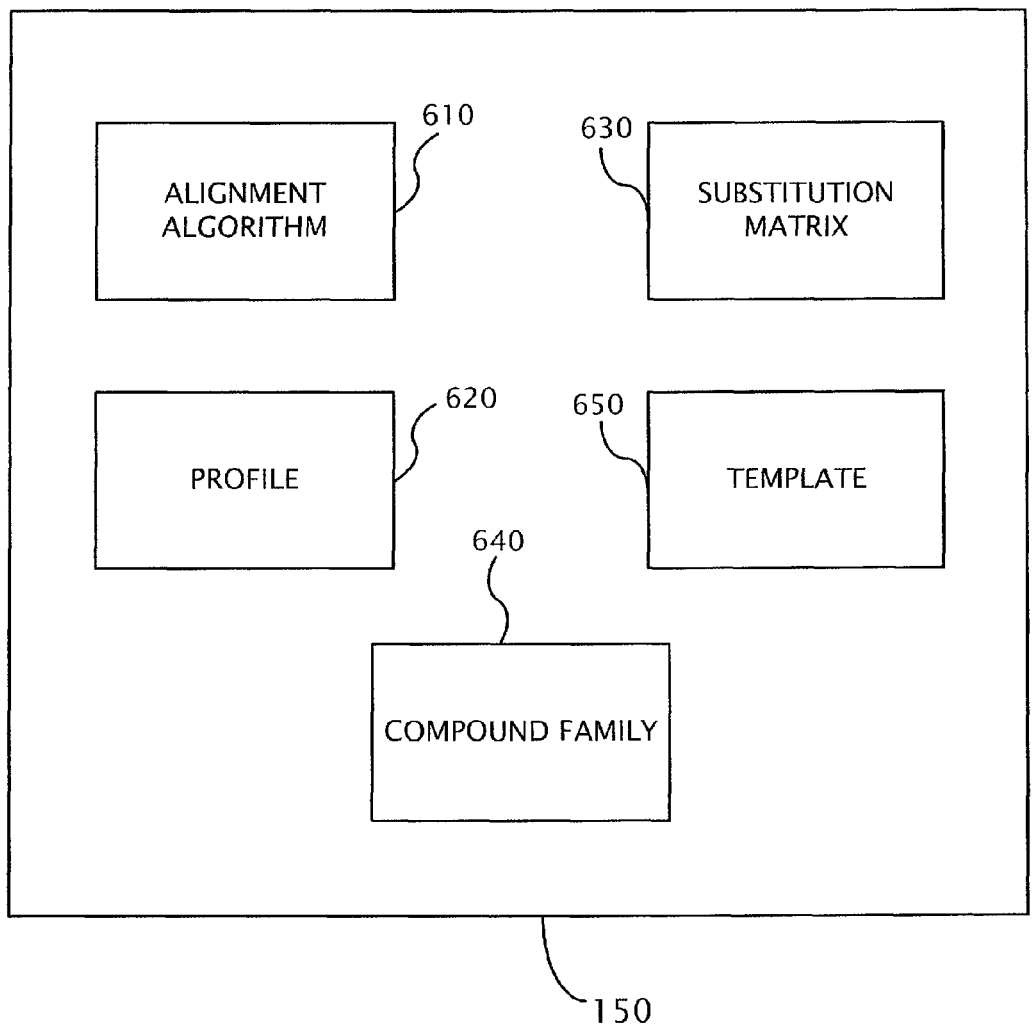
FIG. 6 is a block diagram of an embodiment of a component for identifying chemical compounds.

FIG. 6 shows a block diagram of an exemplary embodiment of the chemical identifier component 150 of system 100. In the depicted embodiment, the component 150 can comprise one or more of the following: an alignment algorithm component 610; a profile component 620; a substitution matrix component 630; a compound family 640; and a template component 650. These components are discussed in more detail below.

Figure 7:
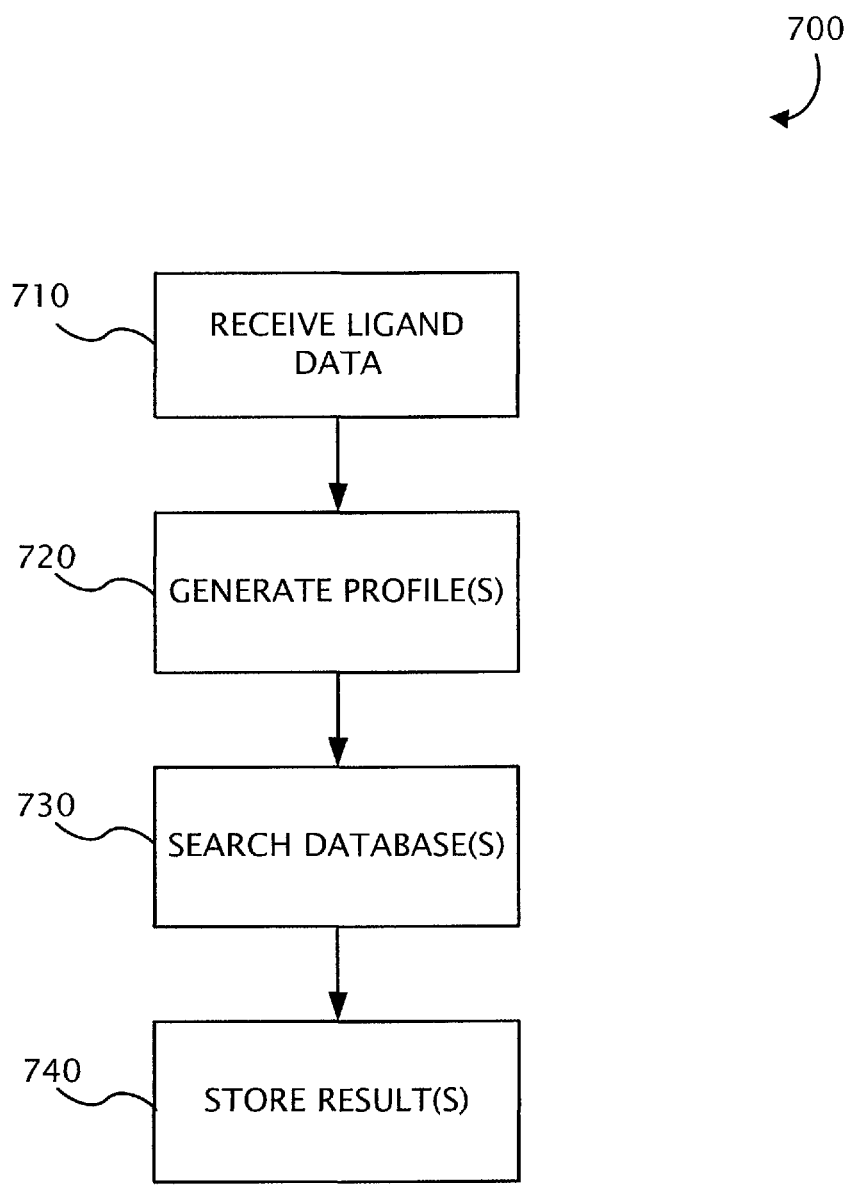
FIG. 7 is a block diagram of an exemplary embodiment of a method for screening chemical compounds.

FIG. 7 is a block diagram of an exemplary embodiment of a method 700 for screening chemical compounds. More particularly, the method 700 can be used to identify ligand homologues by, for example, a system such as system 100. In a method act 710 input ligand data (e.g., structural descriptions of ligands) is received. One or more profiles identifying patches in the input ligand are generated (method act 720), and the chemical database 130 is searched based on the profiles (method act 730). The database 130 comprises descriptions of chemical compounds annotated with force field information (e.g., in one of the formats discussed above). The results of the search can be stored in one or more computer-readable media in a method act 740.

Figure 8:
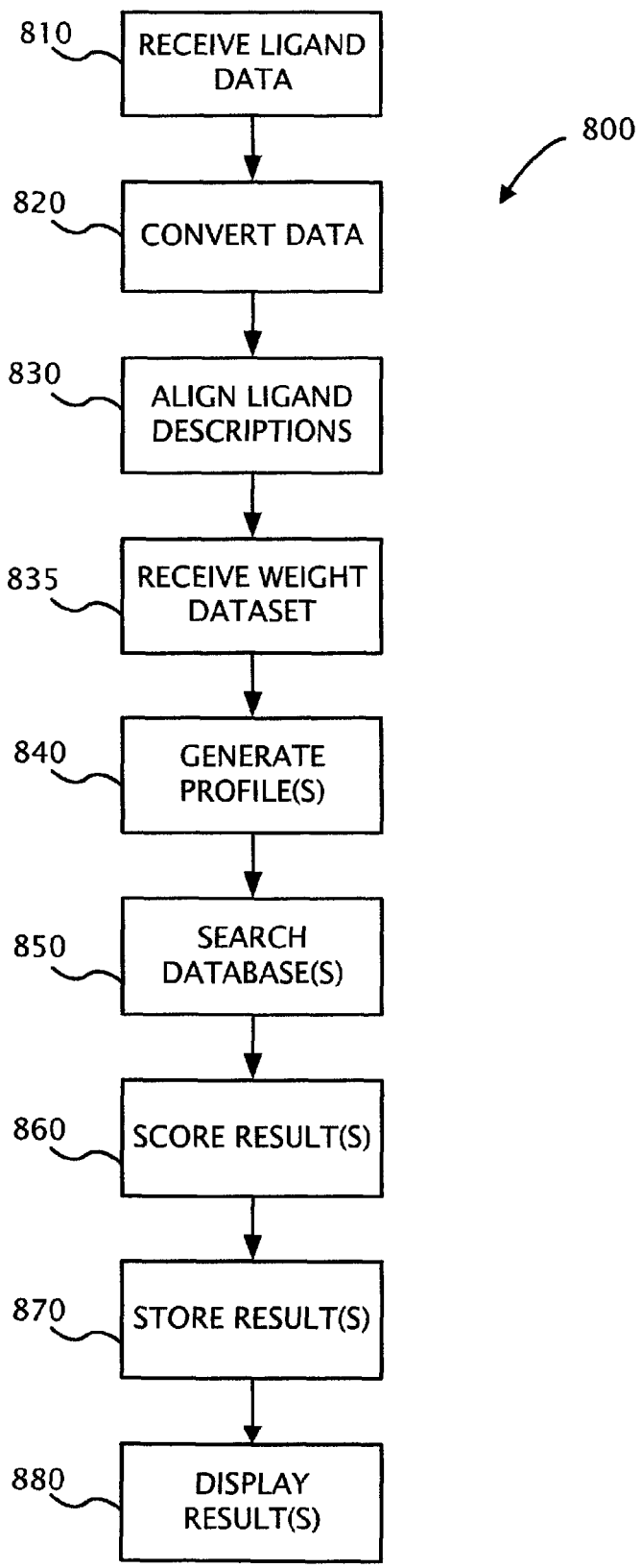
FIG. 8 is a block diagram of an exemplary embodiment of a method for screening chemical compounds.

FIG. 8 shows a block diagram of an exemplary embodiment of a method 800 for screening chemical compounds. In a method act 810, ligand data is received. In some embodiments this data can comprise structural descriptions of one or more input ligands (e.g., in SMILES or another format). Usually, these descriptions are of ligands which interact with a common protein target, and to which other ligands will be compared. In further embodiments, the ligand data further comprises binding affinity information (e.g., $IC_{50}$, Ki and/or pKi values) for one or more of the input ligands with respect to one or more protein targets, and/or binding affinity ranges for various classes of binders (e.g., "good binders," "neutral binders," "bad binders"). Segregating binders by binding affinity information aides understanding which moieties in a given molecule lead to good, bad or neutral binding, as binding affinity is generally related to the atomic composition and construction of a ligand. The binding affinity information can be obtained, for example, from literature, biochemical assays, and/or software models. In some embodiments, one or more default binding affinity ranges can be used. Exemplary binding affinity values are: less than about 20 nM for a "good binder"; between about 20 nM and about 50 nM for a "neutral binder"; and between about 50 mM and about 100 nM for a "bad binder." The ligand data can further comprise a number of desired matches (e.g., a number of ligands identified as having at least some similarities to the input ligands).

In a method act 820, the input ligand structural descriptions can be converted from a first format to a second format using, for example, techniques described above. In some embodiments, the descriptions are converted from SMILES format to FSMILES, SMILESFF and SMILESFFTR formats.

In a method act 830, alignments of two or more descriptions (for example, descriptions in SMILESFFTR format) are performed. In some embodiments this can be done using a sequence alignment algorithm, for example, ClustalW. In particular embodiments the ClustalW algorithm can be modified to: read descriptions in SMILESFFTR format (or another format described herein); adjust gap penalties; and set a default expectation value. An alignment can be performed as a progressive pairwise alignment of input ligands, as further explained below (e.g., with respect to FIG. 8). The aligned descriptions can be used in identifying one or more common chemical moieties (e.g., patches) among the input ligands.

In selected embodiments, alignments of all input ligands are performed with respect to each other. For example, ClustalW can be used to align the entire group of inputs ligands as a whole. Table 6 shows an example of aligned SMILESFFTR descriptions, namely, the descriptions of Table 5. While it can be relatively computationally efficient to align all of the ligands as a whole, in some cases it can be difficult to identify "good patches" and "bad patches" from such an alignment.

TABLE 6

| Description No. | Aligned Sequences |
|---|---|
| 1 | jFjjjyjYKZyyKYDZYDZbbbbbb---------j |
| 2 | ---jMjjYzZ-yKYDZYDZbbbbYCLZbb------ |
| 3 | jjYjZYjZMjjyKYDZYDZbbbbYCLZb-----b- |
| 4 | jjYjZYjZMjjyKYDZYDZbbbbYCLZbYCLZb-- |
| 5 | ---jyYjZjjjyKYDZYDZbbbbbYRZb--YjZj- |
| 6 | ---jjFaYDZ-yKYDZYDZbbbbbbYCL-Z----- |
| 7 | --------yYyZKYDZYDZommoYCLZ------L- |
| 8 | --------MYyZ-YDZYDZommoYCLZ------L- |
| 9 | --------MYyZ-YDZYDZommoYS-Z------L- |
| 10 | --------MYyZ-YDZYDZbbbbYCLZbYCLZb-- |

In further embodiments, input ligands can be divided into two or more groups, and alignments of input ligands can be performed within the groups. For example, in some embodiments the input ligands can be divided into groups of "good binders" and "bad binders" based, for example, on binding affinity information. For a case where the descriptions 1-5 of Table 5 describe "good binders," Table 7 shows alignments of these descriptions. For a case where descriptions 6-10 of Table 5 describe "bad binders," Table 8 shows alignments of those descriptions. Careful comparison of Tables 6, 7 and 8 reveals differences in alignments. While it can be computationally more expensive to align two separate groups of ligands compared to one collective group, this approach can provide more accurate identification of good and bad patches. However, there is also the possibility that a scaffold (backbone) in the sequences will be considered as a good patch among the good binders and a bad patch among the bad binders.

TABLE 7

| Description No. | Aligned Sequences |
|---|---|
| 1 | jFjjjyjYKZyyKYDZYDZbbbbbbj---------- |
| 2 | ----jMjjYzZyKYDZYDZbbbbYC-LZbb------ |
| 3 | jjYjZYjZMjjyKYDZYDZbbbbYC-LZbb------ |
| 4 | jjYjZYjZMjjyKYDZYDZbbbbYC-LZb-YC-LZb |
| 5 | ---jyYjZjjjyKYDZYDZbbbbbY-RZbYjZj--- |

TABLE 8

| Description No. | Aligned Sequences |
|---|---|
| 6 | jjFaYDZyKYDZYDZbbbbbbYCLZ------- |
| 7 | ---yYyZ-KYDZYDZommo--YCLZ------L |
| 8 | ---MYyZ--YDZYDZommo--YCLZ------L |
| 9 | ---MYyZ--YDZYDZommo--YS-Z------L |
| 10 | ---MYyZ--YDZYDZbbbb--YCLZbYCLZb- |

In additional embodiments alignments of three input ligand groups are performed: one alignment for a group of "good binders," one alignment for a group of "bad binders" and another alignment for all of the ligands. While this is generally the computationally most expensive approach, it can provide accurate identification of good and bad patches, as well as identification of a backbone in the input ligands.

In some embodiments, a weight dataset is received in a method act 835, as explained in more detail below. The weight dataset can be used, for example in a method act 840, in generating one or more profiles based on at least some of the input ligand structural descriptions. Generally, a profile describes one or more patterns in at least some of the input descriptions in terms of one or more properties. Various embodiments use one or more techniques to identify patches in aligned ligand descriptions. Particular embodiments use a Hidden Markov Model to generate one or more profiles based on input ligand structural descriptions.

In particular embodiments, a profile can comprise one or more patches and weights for the patches. A profile can be created based on alignments for a full set of input ligands (a "consensus profile") or for a subset of input ligands (e.g., for "good binders" or "bad binders"). A weight for a given patch can be determined at least in part by factors such as the number of alignments in which the patch occurs and the length of the patch. For example, a patch which is present in most or all pairwise ligand alignments can be considered the most significant patch for a set of ligands, and this can be reflected in a profile by assigning a weight (e.g., a large weight) to that patch. A patch present in, for example, about half of the pairwise alignments can be assigned a medium weight, while a patch appearing in relatively few alignments (e.g., two or fewer alignments) can be assigned a small weight. Further embodiments can employ additional weighting schemes with various ranges of weights. Additionally, weights for patches can also be assigned based on alignments of, for example, two, four, or more ligands. Some embodiments can assign higher scores to longer patches and smaller scores to shorter patches (or vice versa).

Figure 9:
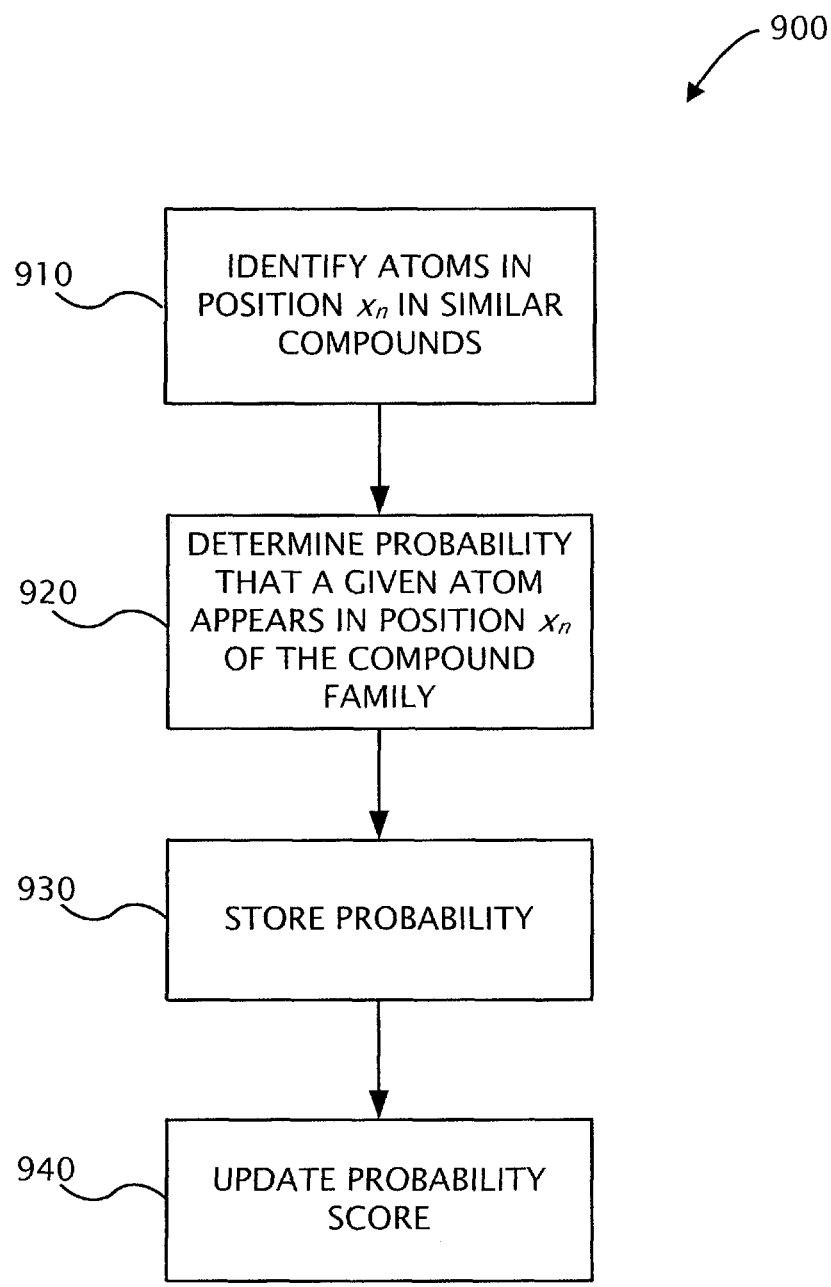
FIG. 9 is a block diagram of one embodiment of a method for creating or revising a weight dataset.

In some embodiments a weight dataset (e.g., a substitution matrix) can be generated for use in evaluating one or more profiles. FIG. 9 shows a block diagram of one embodiment of a method 900 which uses a learning-based approach for creating or revising a weight dataset for use with the method 800. Given a family of compounds (e.g., structural descriptions of two or more ligands, usually ligands that can perform a similar function), atoms occupying a position $x_n$ in each of the compounds are identified (method act 910). The position $x_n$ can be, for example, a particular position which complements the ligand and a protein target. By examining occurrences of different atoms in structures of the family members, the probability that a given atom at the position $x_n$ can be replaced with another atom is determined (method act 920). For example, the probability of replacing a carbon atom (having sp3 hybridization, a radius of 1.7 Angstroms, and a charge of 0.9 esu) with a nitrogen atom (having sp2 hybridization, a radius of 1.5 Angstrom, and a charge of 0.2 esu) can be determined. This probability can be stored in one or more computer-readable media (method act 930) in, for example, a matrix or other data structure. In some embodiments, a weight dataset that was created based on a family of compounds can be updated in a method act 940 if members of that family change or if a new member is added to the family.

Returning to FIG. 8, in some embodiments, as part of profile generation (method act 840), a weight for a patch can be obtained or modified by comparing the patch (e.g., atom-by-atom for each atom in the patch) to the weight dataset. For example, if a patch is similar to the weight dataset, the patch's score in the profile can be increased. If the patch is dissimilar to the weight dataset, the patch's score in the profile can be decreased. In further embodiments, multiple levels of similarity can be used when comparing a patch to a weight dataset.

In further embodiments, a template describing a common set of factors among known ligands (e.g., known inhibitors to a protein target for which compounds will be screened) can be used as part of profile generation (method act 840). The template can comprise information such as: which groups of atoms are co-located at a given distance from a benzene ring of a ligand in the ligand family; the coordinate geometry of one part of a ligand molecule relative to another part of the ligand molecule; and charges and sizes of atoms that are aligned in the same phase of a ligand-protein target interface. Information in the template can be used to determine a weight for one or more patches in a profile.

Figure 10:
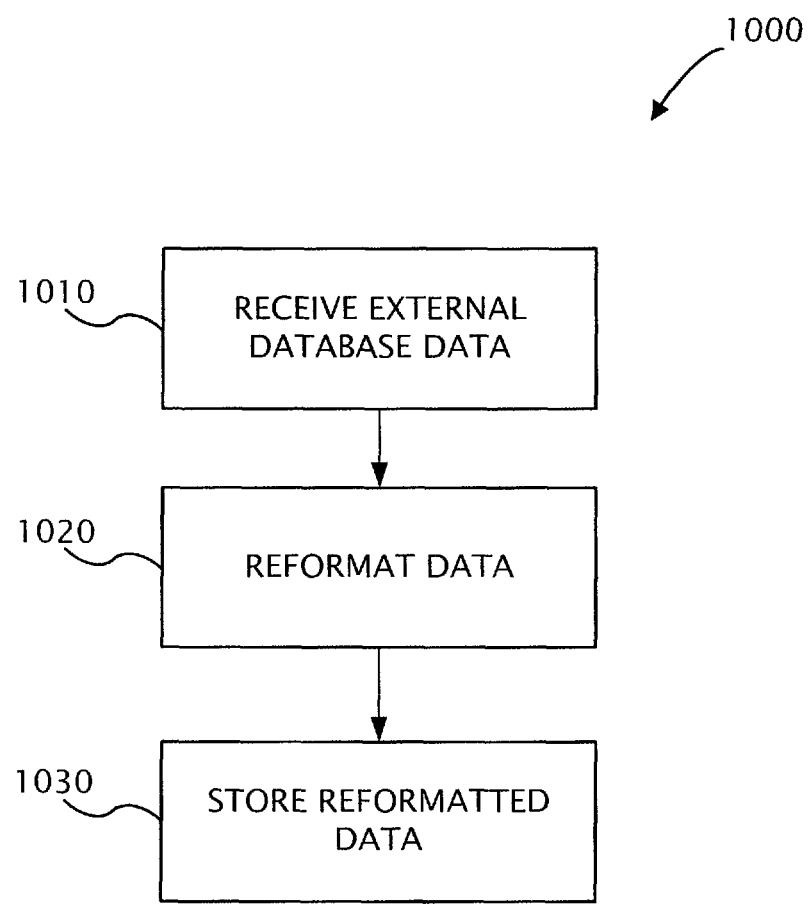
FIG. 10 shows a block diagram of an embodiment of a method for creating a database.

The one or more profiles can be used to search the one or more chemical databases 130 (method act 850). The databases 130 can comprise information from one or more external databases, for example, commercial, governmental or academic databases, such as the Maybridge Chemical Database available from the Maybridge Chemical Company. In at least some embodiments, portions of the databases 130 are created according an embodiment of an exemplary method 1000, a flowchart of which appears in FIG. 10. In a method act 1010, data from an external database is received. In some embodiments the received data is in a structure data file (SDF) format, but other formats can also be used. At least some of the data can be reformatted (method act 1020), for example, into SMILES format, FSMILES format, SMILESFF format and/or one or more other formats. The reformatted data can be stored (method act 1030) in the databases 130 or in a flat file. In further embodiments additional information can be included in the databases 130, for example, a database identifier for correlating the reformatted data with information in the external database, International Union of Pure and Applied Chemistry (IUPAC) names, and/or Lipinksi druggability parameters for one or more compounds. The databases 130 can be implemented using, for example, an Oracle database or other type of database or in a flat file.

When searching the chemical databases 130, one or more chemical compounds are identified in the database that have one or more patches contained in the profile. In method act 860, the identified compounds can be assigned a score based at least in part on their respective patches and the effects that the patches are considered to have on binding to a protein target. For example, in some embodiments a compound can receive: a score of +1 if it features a "good" patch that has a positive effect on binding to the protein target; a score of 0 if it features a "neutral" patch that does not effect binding; and a score of −1.0 if it features a "bad" patch that has a negative effect on binding to the protein target. In cases where a compound comprises more than one patch, the scores for the individual patches of the compound can be summed to create a score for the compound. Results of the searching and scoring (method acts 850, 860) can be stored in one or more computer-readable media (method act 870) and or displayed (method act 880). The identified compounds output component 140 of system 100 can display at least some of these results. In some embodiments search results are displayed based at least in part on their scores. For example, the highest-scoring compounds from the search results can be displayed to a user. In further embodiments, both lowest- and highest-scoring compounds can be displayed with their respective scores. Embodiments of displayed search results are described in more detail below.

Experimental Results

In one set of experiments, a class of inhibitors to a protein target was chosen, and techniques described herein were used to identify relatively similar compounds from a diverse library of chemical compounds. More specifically, a known class of Cox-2 inhibitors was selected, whose members are often used as pain killers. The four molecules of this class bind with varying selectivity to the Cox-2 enzyme and are shown in Table 9 with their respective $IC_{50}$ values.

TABLE 9

| Cox-2 Inhibitor | $IC_{50}$ (mmol/L) | Cox-2 selectivity ratio of $IC_{50}$ (Cox-1/Cox-2) |
|---|---|---|
| Etoricoxib | 1.10 ± 0.10 | 106.0 |
| Rofecoxib | 0.53 ± 0.02 | 35.0 |
| Valdecoxib | 0.87 ± 0.11 | 30.0 |
| Celecoxib | 0.87 ± 0.18 | 7.6 |

Figure 11:
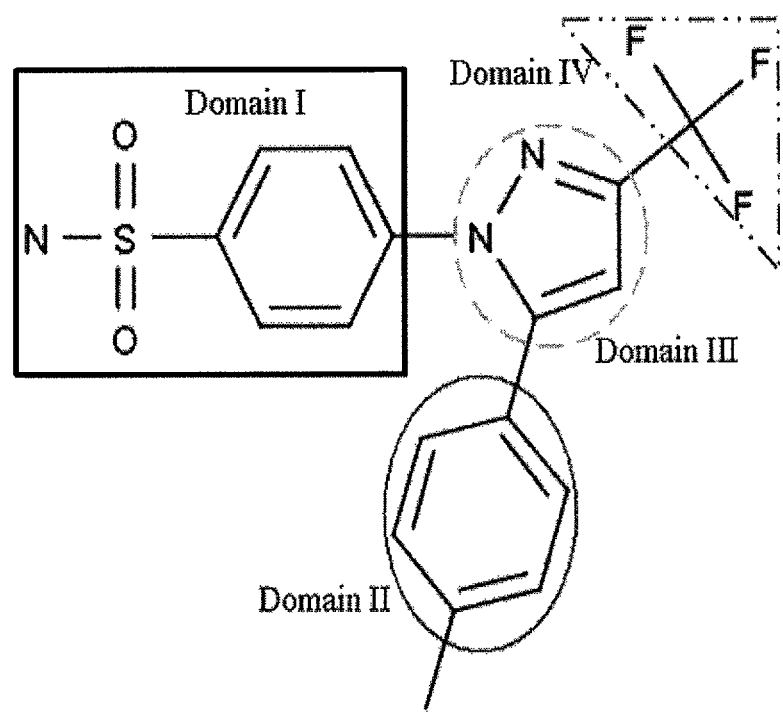
FIG. 11 depicts the structure of Celecoxib.
Figure 12:
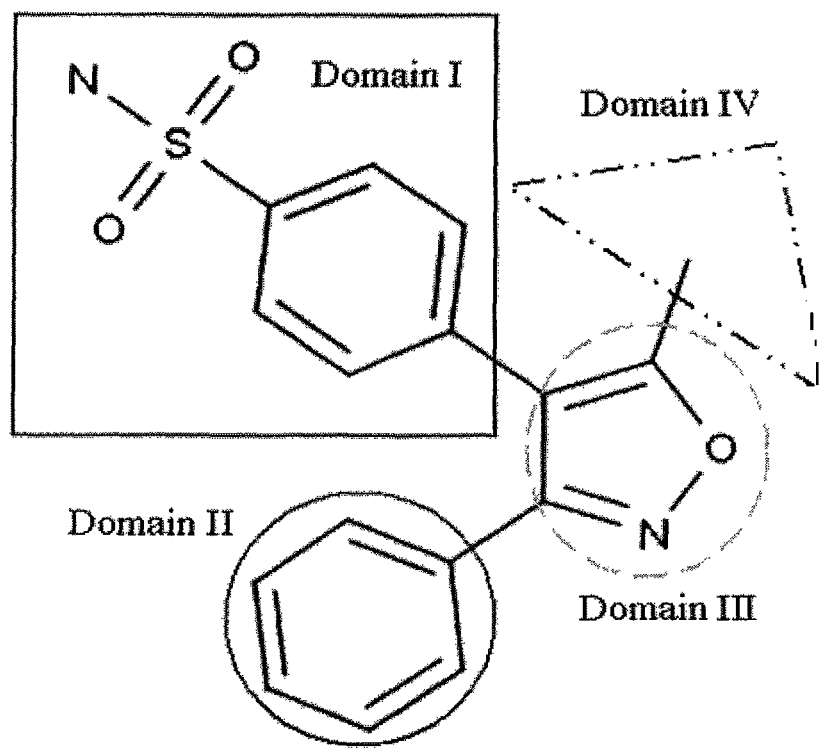
FIG. 12 depicts the structure of Valdecoxib.

Table 9 also lists the binding selectivity of each inhibitor with respect to the Cox-1 enzyme. While Valdecoxib and Celecoxib have about the same binding affinity with respect to Cox-2, they have unequal binding affinity with respect to Cox-1. The structure of Celecoxib appears in FIG. 11, while the structure of Valdecoxib is shown in FIG. 12. For comparison, in each of FIGS. 11 and 12 Domains I-IV are marked, and visual examination, as well as the chemical similarity index of PubChem, suggest that these two molecules are no more than about 60% similar in structure. For example, in each molecule the atoms in the ring position of Domain II differ, and Domain IV is absent in Valdecoxib. Although both molecules have similar backbone structures (benzene and five-member pyrazol/oxazol rings), visual inspection suggests that Celecoxib has additional fluorine pendant groups and a higher nitrogen content than Valdecoxib.

The present set of experiments examined whether the structures of Celecoxib and Valdecoxib, being relatively distantly similar but having equivalent binding affinity to a selected protein target, can be screened using technologies described herein. For input ligands, a set of molecules similar to Celecoxib (greater than 90% similar, according to PubChem) were provided to a system similar to system 100. Using a method similar to method 800, chemical homologues of input ligands were identified and assigned scores. FIG. 13 shows three chemical homologues identified by the method, along with their respective assigned scores (a higher score indicating a better match with the input ligands). Celecoxib was identified with a high score of 15, but Valdecoxib was also identified as a relatively well matching chemical homologue. Thus, although Valdecoxib was no more than 60% similar to Celecoxib (and, correspondingly, no more than about 60% similar to the input ligands), Valdecoxib was selected as a relatively good "hit" by the system.

Reverse validation was performed with molecules similar to Valdecoxib as input ligands. FIG. 14 shows the results of the reverse validation, which lists both Valdecoxib and Celecoxib as hits.

An additional set of experiments considered inhibitors of thymidylate kinase (a therapeutic protein target for tuberculosis), such as azido-thymine mono phosphate (AZTMP). In this case, eight inhibitors were identified from literature (AZTMP and seven other synthesized analogues), which are shown in FIG. 15 as Inputs 1-8. Molecules 1-5 from FIG. 15 were used as input ligands in a method similar to method 600. The hits appear in the rightmost column of FIG. 15 labeled "Output Homologues from Maybridge." One hit, 1-5 anhydrohexitol, is Input 6 from FIG. 15. The other three hits, in which the substructure of a phosphate group is replaced by a sulphonate group, can be used as leads in the further fine-tuning of designer thymidylate kinase inhibitors.

In a third set of experiments, techniques described herein were used to identify chemical homologues to known inhibitors to Cox-1 and Cox-2 based on profile searches against the Maybridge database. As shown in Table 10, these protein targets were selected for arthritis and inflammation, respectively. The protein target-inhibitor complex for each protein target was collected from reported literature, and this information also appears in Table 10, along with binding affinity information for the inhibitors and the key pharmacological actions of the inhibitors.

bridge database was searched. Output homologues for each case are shown in FIGS. 16 and 17.

Exemplary Embodiments of User Interfaces

Figure 18:
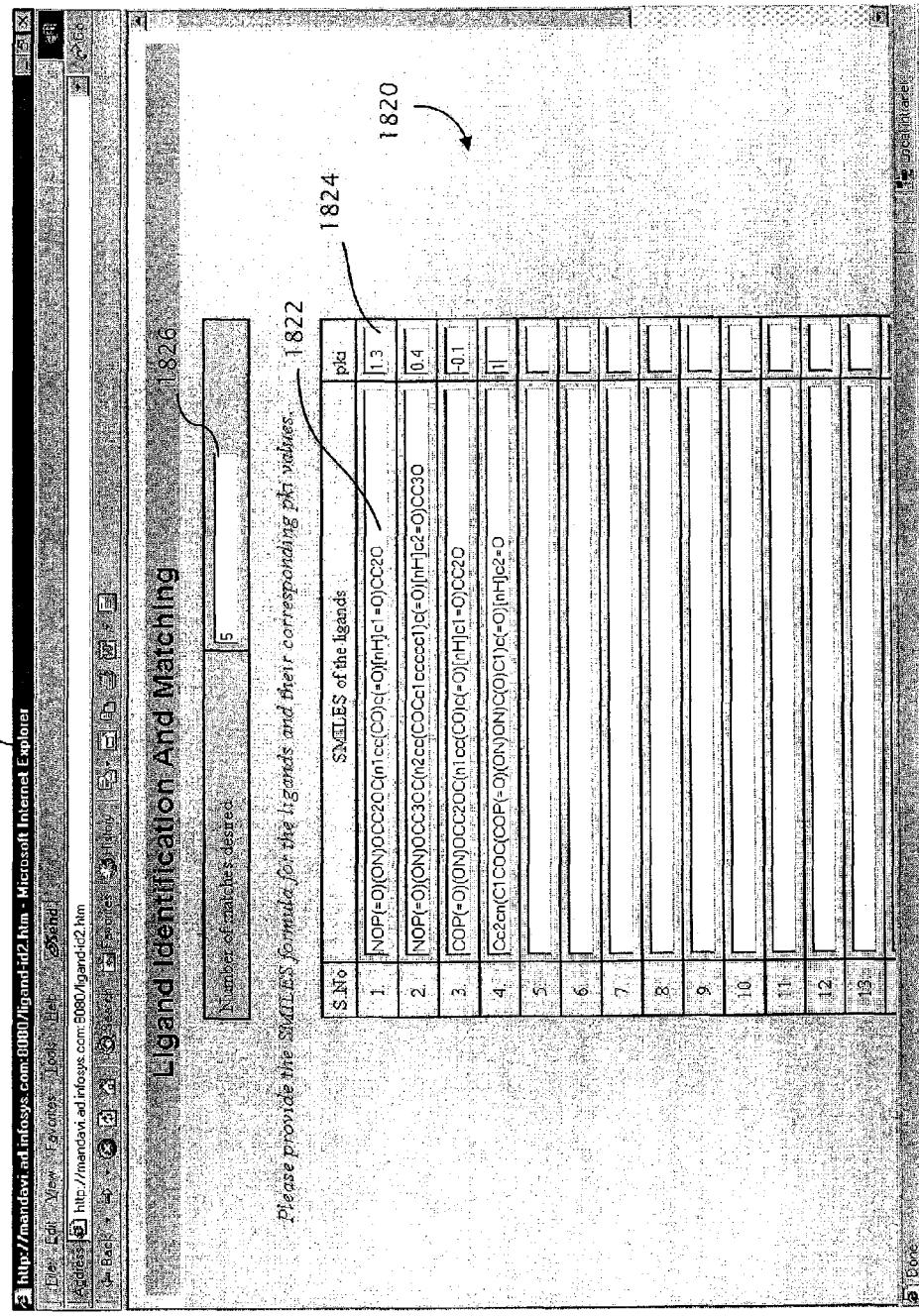
FIG. 18 is a diagram of an exemplary embodiment of a user interface.

As explained above, the system 100 can comprise a UI component 170. FIG. 18 shows one embodiment of the UI component 170 comprising a window 1810. In the depicted embodiment the window 1810 is a web browser window, but in further embodiments one or more other applications can be used. The window 1810 can display input fields 1820 for receiving information for input ligands. This information can comprise one or more structural descriptions of the ligands, for example in SMILES format or other formats (e.g., description 1822). In further embodiments the information can also comprise affinity binding information for the input ligands (e.g., pKi value 1824). A field 1826 can receive an indication of how many output ligands a user desires. In further embodiments, one or more additional fields (not shown) can receive indicators (e.g., pKi values) of one or more ranges for different categories of binders, such as "good," "bad" and/or "neutral" binders. The embodiment of the UI component 170 appearing in FIG. 18 is a graphical user interface (GUI), but additional embodiments can comprise other types of user interfaces.

FIG. 19 shows a further embodiment of the UI component 170 comprising a window 1910, which can be a window for a web browser or other application. The window 1910 can display results of processing input ligands according to a method such as the method 600. The results can comprise structural descriptions of one or more output ligands, such as description 1912, as well as one or more scores associated with the output ligands, such as score 1914.

Figure 20:
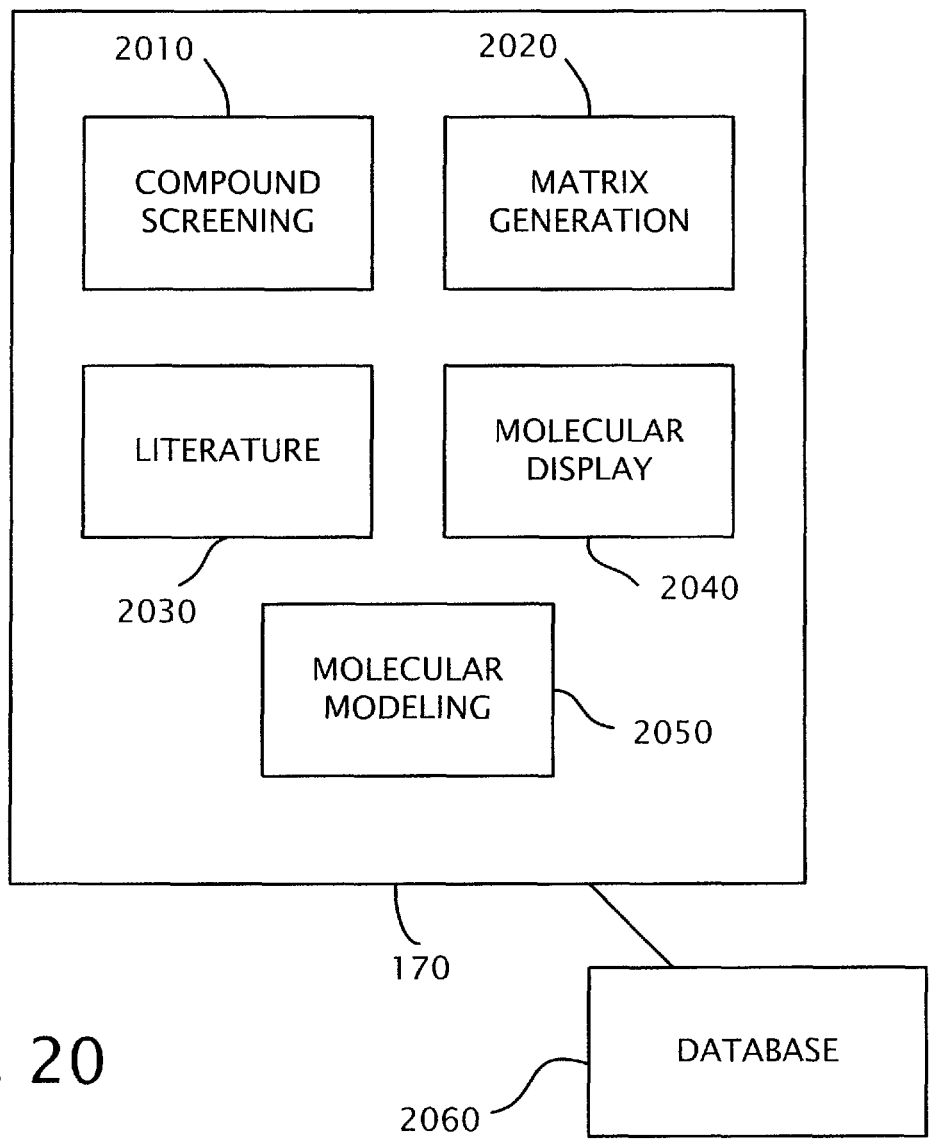
FIG. 20 is a block diagram of an exemplary embodiment of a user interface component.

FIG. 20 depicts a block diagram of one exemplary embodiment of the UI component 170. The component 170 can comprise a compound screening component 2010, a matrix generation component 2020, a literature component 2030, a molecular display component 2040, and a molecular modeling component 2050.

The compound screening component 2010 can be used to identify one or more candidate compounds based, for example, on a set of inputs (e.g., input compounds). The component 2010 can use one or more methods or systems

TABLE 10

| Disease | Protein Target Name | Known Inhibitor/Drug | Binding Affinity [$K_i$, $pK_i$, $IC_{50}$] (mmol/L) | Pharmacological Action [MeSH] |
|---|---|---|---|---|
| Arthritis | Cyclooxygenase-2 [COX-2] EC 1.14.99.1 1CX2 (c) | Rofecoxib[Vioxx] Celecoxib[Celebrex] Valdecoxib[Bextra] | $IC_{50} = 0.53 \pm 0.02$ $IC_{50} = 0.87 \pm 0.18$ $IC_{50} = 0.87 \pm 0.11$ | Cyclooxygenase Inhibitors |
| Inflammation | Cyclooxygenase-1 [COX-1] EC 1.14.99.1 1PRH(s), 1PTH(c), 1CQE (c) | Aspirin Diclofenac Etodolac | $IC_{50} = 0.15 \pm 0.04$ $IC_{50} = 9.0 \pm 2.5$ $IC_{50} = 0.19 \pm 0.02$ | Anti-Inflammatory Agents, Non-Steroidal |

For Cox-1, compounds with a similarity to aspirin of greater than 90% were selected from the PubChem database and used as input data for a method similar to method 600. These input data appear in FIG. 16. For Cox-2, compounds with a similarity to Rofecoxib (known commercially as Vioxx) of greater than 90% were selected from the PubChem database and used as input data for a method similar to method 600. These input data appear in FIG. 17. For both cases, profiles of the input data were generated, and the May-described above. The matrix generation component 2020 can receive inputs for creating the substitution matrix 630. The literature component 2030 can be configured to provide information regarding one or more chemical compounds, for example, identified candidate compounds and/or input compounds. In some embodiments information displayed by the literature component can be provided by one or more databases 2060, for example, the PubMed literature database. The molecular display component 2040 can be configured to display graphic and text information regarding one or more chemical compounds, for example, identified candidate compounds and/or input compounds. The molecular modeling component 2050 can be configured to allow a user to draw one or more chemical structures and convert the drawings into various formats, for example, one or more of the formats described herein. In some embodiments, the modeling component 2050 is implemented using a version of Marvin-Sketch.

Figure 21:
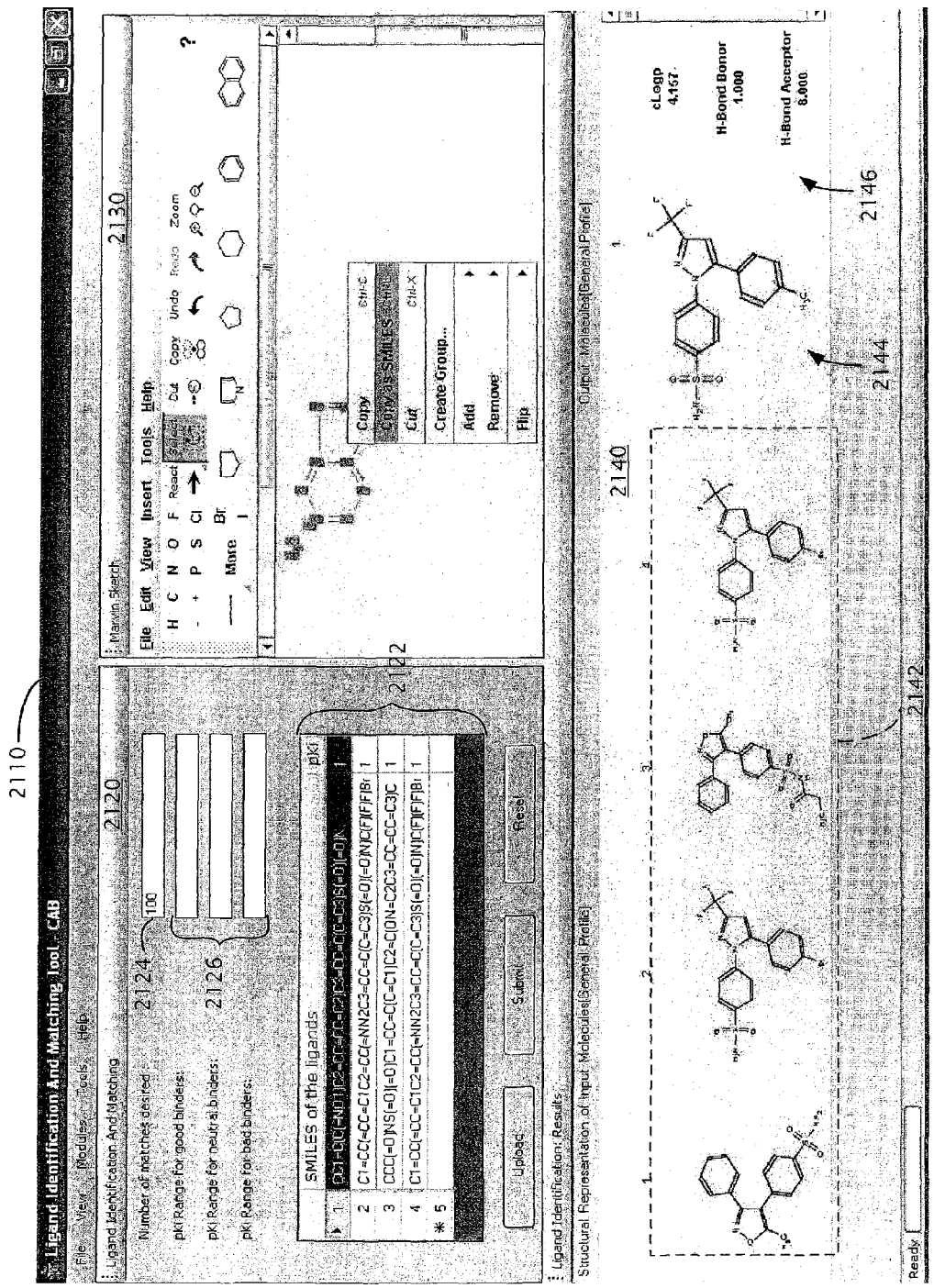
FIG. 21 is a diagram of an exemplary embodiment of a user interface.

FIG. 21 shows a diagram of one embodiment of a UI comprising at least some of the features appearing in FIG. 20. A window 2110 comprises subsections 2120, 2130, 2140. In this embodiment, subsections 2120, 2140 comprise portions of the compound screening component 2010. A field 2122 can receive descriptions of input ligands for which matches are desired. In FIG. 21 these descriptions are provided in SMILES format, along with respective binding affinity information (here, pKi values) of the ligands. A field 2124 can receive an indication of a number of desired matches for the input ligands, while one or more fields 2126 can receive binding affinity information for various classes of binders (e.g., "good," "neutral" and/or "bad"). The subsection 2140, in conjunction with the molecular display component 2040, displays structural graphic representations 2142 of the input ligands (input molecules), as well as structural graphic representations 2144 of one or more identified candidate compounds (output molecules). In some embodiments, information about the one or more identified candidate compounds (e.g., Lipinski parameters) can also be displayed as text, as shown by text 2146. The subsection 2130 shows an implementation of the molecular modeling component 2050 using MarvinSketch. Structures modeled using subsection 2130 can be converted to SMILES format and placed in the field 2122 as an input ligand.

Figure 22:
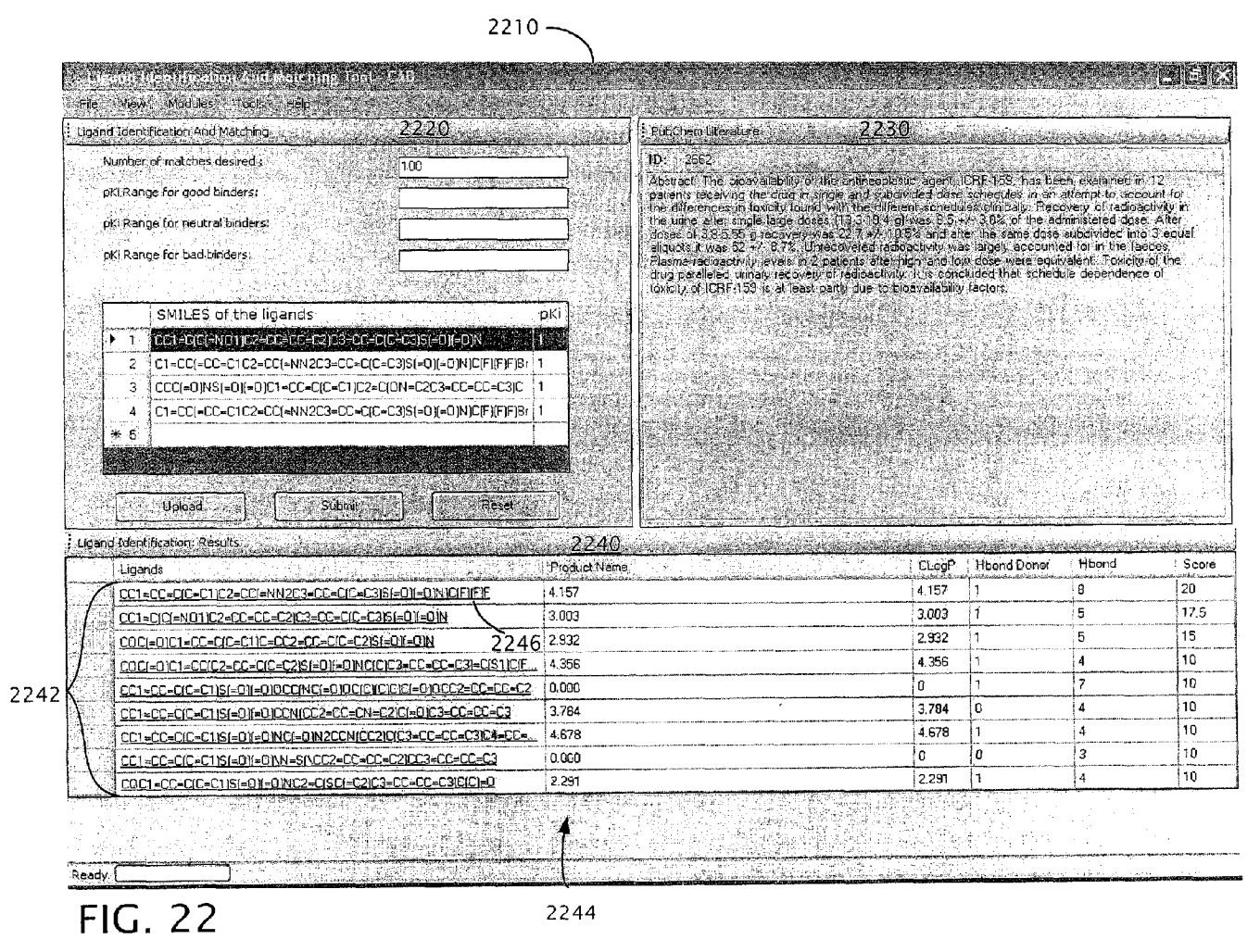

FIG. 22 shows a diagram of another exemplary embodiment of a UI comprising at least some of the features appearing in FIG. 20. In this embodiment, a window 2210 comprises subsections 2220, 2230, 2240. In this embodiment, subsections 2220, 2240 comprise portions of the compound screening component 2010, with subsection 2220 being configured similarly to subsection 2120 of FIG. 21. Subsection 2240 displays structural text descriptions 2242 and additional text information 2244 of one or more identified candidate components. Subsection 2230 shows an implementation of the literature component 2030, in this case displaying an abstract from the PubChem database. In the depicted embodiment, the structural text descriptions 2242 can comprise one or more hyperlinks, such as hyperlink 2246. A hyperlink can connect a structural text description to, for example, an entry from the literature component 2030, a structural graphic representation, or other information.

In at least some embodiments of the UI component 170, identified candidate compounds can be viewed for additional structural and chemical attributes using one or more of the components 2010, 2020, 2030, 2040, 2050. Various elements appearing in the embodiments of FIGS. 21 and 22 can be used in combination with each other.

In some embodiments at least a portion of the UI component 170 can be implemented using Microsoft Composite UI Application Block (CUIAB) NET 2.0 Framework. Further embodiments can be implemented using other technologies.

Although various embodiments of the UI component 170 are described herein as being used in conjunction with the system 100, in some embodiments they can also be used with other systems.

Exemplary Network Environments

Any of the aspects of the technologies described above may be performed using a distributed computer network.

Figure 23:
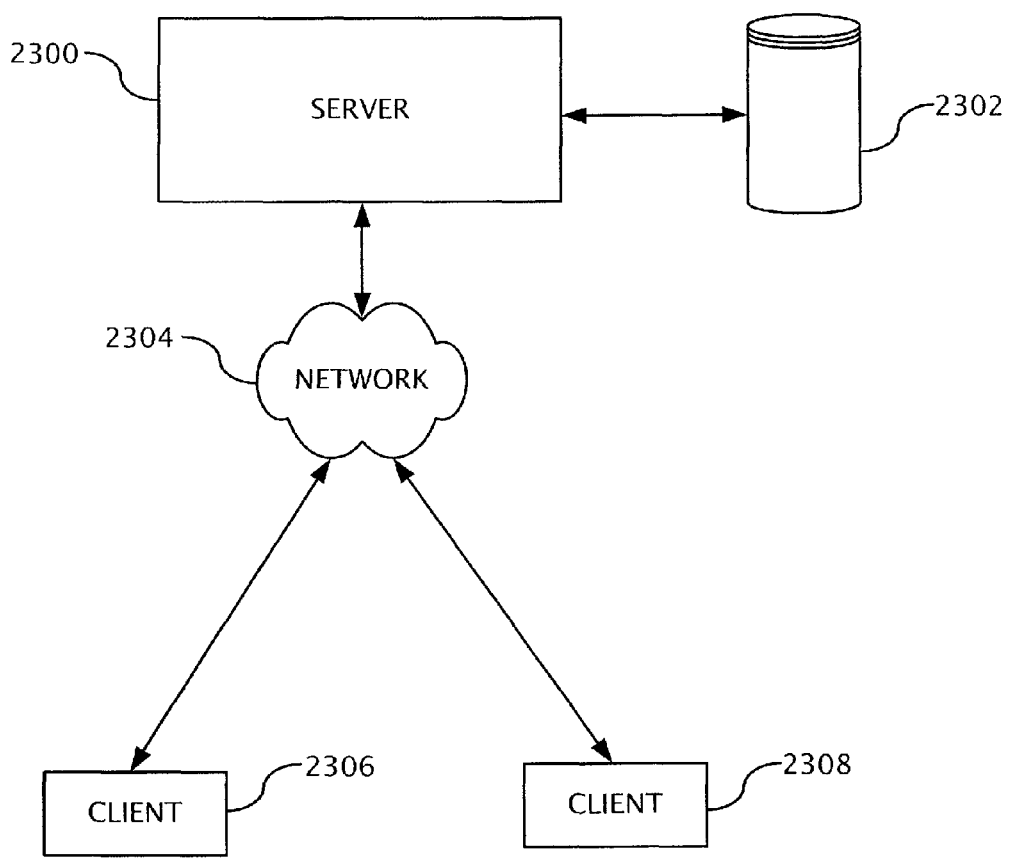
FIG. 23 is a schematic block diagram of a network as can be used to perform any of the disclosed methods or to generate any of the disclosed screening results.

FIG. 23 shows one suitable exemplary network. A server computer 2300 can have an associated storage device 2302 (internal or external to the server computer). For example, the server computer 2300 can be configured to generate any of the disclosed screening method embodiments or any of the data format conversion embodiments. The server computer 2300 can be coupled to a network, shown generally at 2304, which can comprise, for example, a wide-area network, a local-area network, a client-server network, the Internet, or other suitable network. One or more client computers, such as those shown at 2306, 2308, may be coupled to the network 2304 using a network protocol. The work may also be performed on a single, dedicated workstation, which has its own memory and one or more CPUs.

Figure 24:
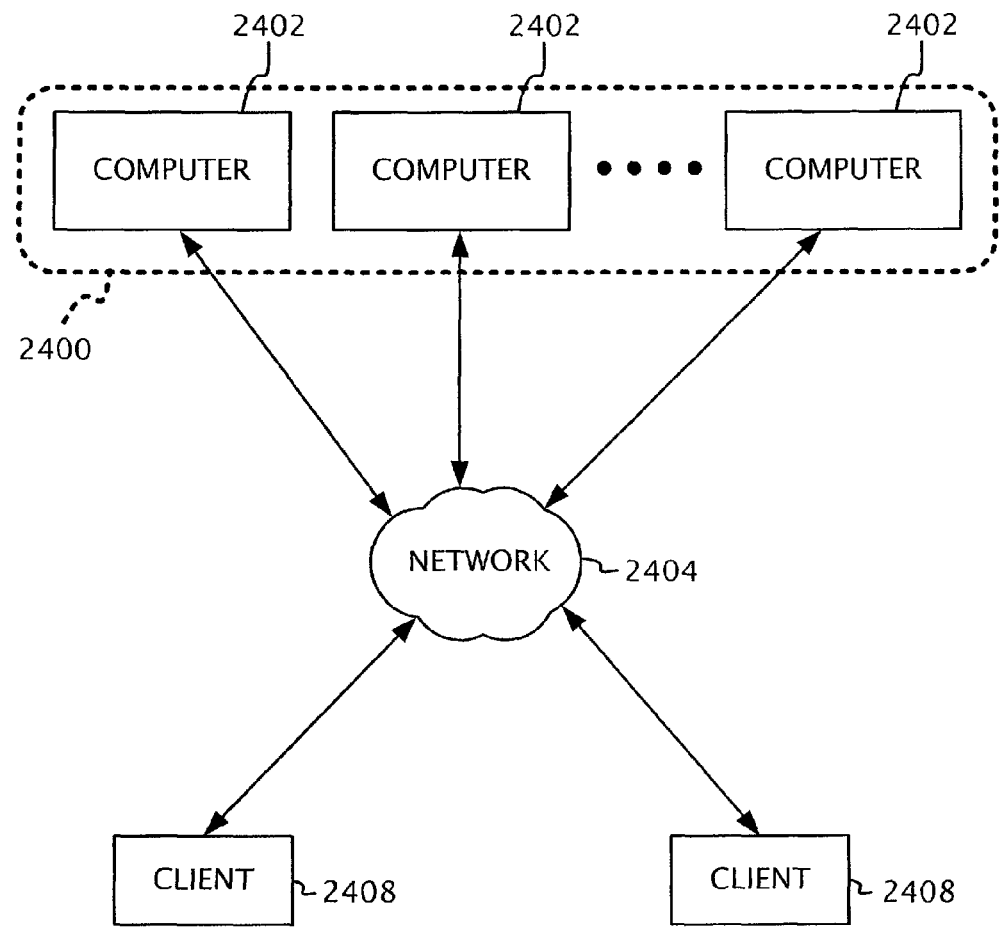
FIG. 24 is a schematic block diagram of a distributed computing network as may be used to perform any of the disclosed methods or to generate any of the disclosed screening results.

FIG. 24 shows another exemplary network. One or more computers 2402 communicate via a network 2404 and form a computing environment 2400 (for example, a distributed computing environment). Each of the computers 2402 in the computing environment 2400 can be used to perform at least a portion of the screening process. The network 2404 in the illustrated embodiment is also coupled to one or more client computers 2408.

Figure 25:
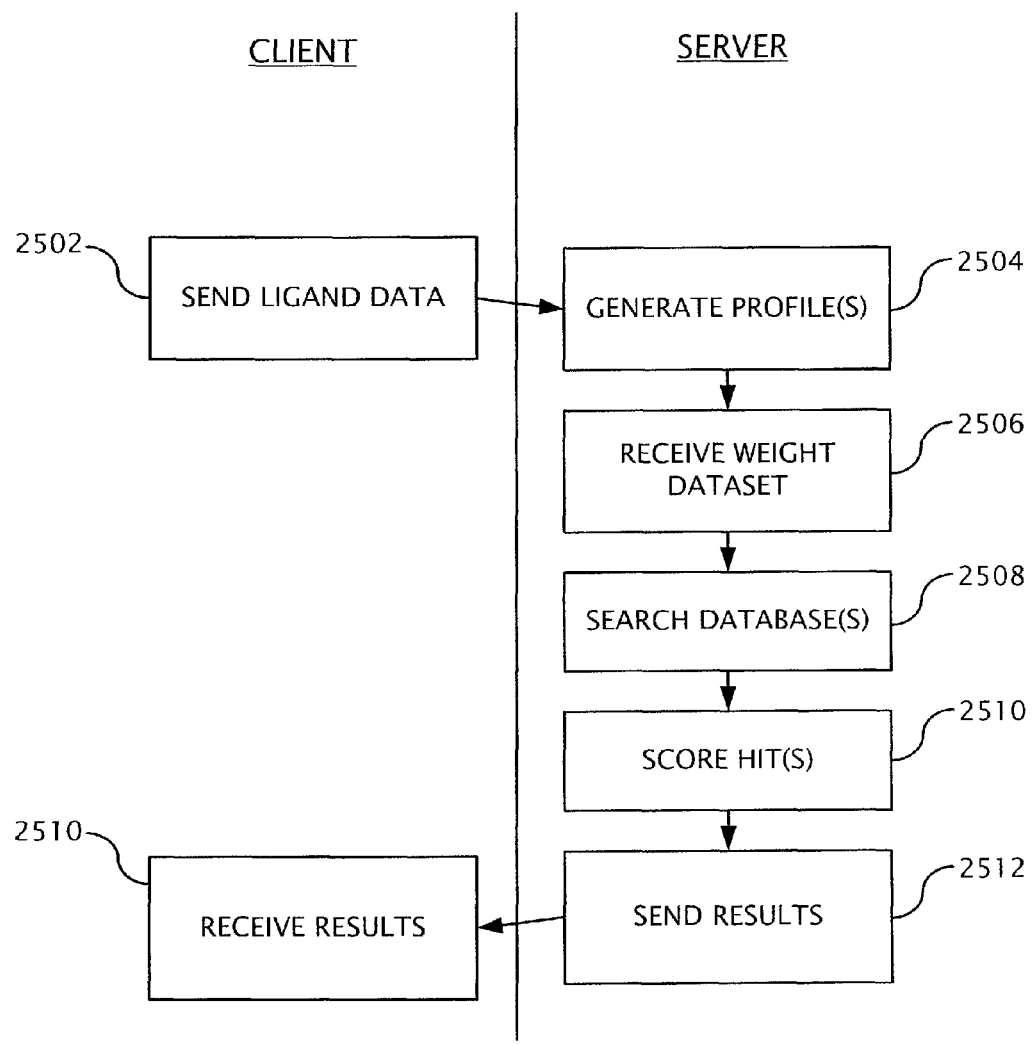
FIG. 25 is a flowchart illustrating how an embodiment of the disclosed screening results can be generated in the network of FIG. 23 and FIG. 24.

FIG. 25 shows that compounds can be screened using a remote server computer (such as the server computer 2300 shown in FIG. 23) or a remote computing environment (such as the computing environment 2400 shown in FIG. 24) in order to generate screening results according to the disclosed technology. At method act 2502, for example, the client computer sends the ligand data to the remote server or computing environment. In method act 2504, one or more profiles are generated by the remote server or by respective components of the remote computing environment. In method act 2506, one or more databases are searched using the generated profiles. At method act 2508, the remote server or computing environment sends the search results to the client computer, which receives the results at method act 2510.

In some embodiments, at least some of the technologies described above can be implemented using components that combine one or more aspects of a thin client, a thick client, and a web service. For example, a "smart client" can be implemented using Microsoft.NET 2.0 technology. Using a smart client, a client computer can be updated when the client computer is synchronized with a server, for example.

In view of the many possible embodiments to which the principles of the disclosed technologies may be applied, it should be recognized that the illustrated embodiments are only preferred examples of the technologies and should not be taken as limiting the scope of the invention. Rather, the scope of the invention is defined by the following claims. We therefore claim as our invention all that comes within the scope and spirit of these claims.

We claim:

1. A method of screening a database of molecules to identify leads for treating a disease, the method comprising:
generating, using a computer, from aligned structural descriptions of a set of input ligands and from binding affinity data for the set of input ligands for a target protein known to be associated with the disease, a profile comprising ASCII structural descriptions of one or more patches in the set of input ligands;
identifying, using the computer, a set of one or more leads for treating the disease from a database, the identifying based at least in part on the profile, wherein the database comprises ASCII structural descriptions of a plurality of molecules, the ASCII structural descriptions of the plurality of molecules comprising force field information for one or more atoms described in the ASCII structural descriptions of the plurality of molecules, the identifying comprising comparing the ASCII structural descriptions of the plurality of molecules with the ASCII structural descriptions of the one or more patches, the ASCII structural descriptions of the one or more leads for treating the disease comprising the ASCII structural description of at least one of the one or more patches; and storing the ASCII structural descriptions of the set of one or more leads for treating the disease in one or more computer-readable media.

2. The method of claim 1, wherein generating a profile comprises:
performing one or more pairwise sequence alignments of the ASCII structural descriptions of the input ligands to generate the aligned structural descriptions; and
identifying one or more patches in the input ligands based on the one or more pairwise sequence alignments.

3. The method of claim 2, wherein generating a profile further comprises assigning a score to an identified patch.

4. The method of claim 3, wherein the assigned score is based at least in part on the number of input ligands in which the identified patch occurs.

5. The method of claim 2, wherein the binding affinity data comprises a first binding affinity range and a second binding affinity range and the performing one or more pairwise sequence alignments of the ASCII structural descriptions of the input ligands comprises:
performing a first set of pairwise sequence alignments among a first subset of the input ligands having binding affinities within the first binding affinity range; and
performing a second set of pairwise sequence alignments among a second subset of the input ligands having binding affinities within the second binding affinity range, wherein the first and second subsets contain no common input ligands.

6. The method of claim 5, wherein performing one or more pairwise sequence alignments of ASCII structural descriptions of the input ligands further comprises performing a third set of pairwise sequence alignments among a third subset of the input ligands, the third set comprising ligands from the first and second subsets.

7. The method of claim 1, wherein identifying selecting the set of one or more leads for treating the disease from a database further comprises assigning scores to one or more chemical compounds in the database based on patches in the one or more chemical compounds in the database, the patches being identified in the profile, wherein the score assigned to a chemical compound is increased if a patch in the chemical compound has a positive effect on binding to the target protein and decreased if the patch in the chemical compound has a negative effect on binding to the target protein.

8. The method of claim 7, further comprising ordering the one or more chemical compounds of the identified selected set based on the scores assigned to the one or more chemical compounds of the identified set.

9. The method of claim 1, wherein the ASCII structural descriptions of the one or more patches and the ASCII structural descriptions of the plurality of molecules comprise sequences of one or more single-letter atom type notations.

10. The method of claim 1, wherein the set of input ligands are inhibitors of the target protein known to be associated with the disease.

11. The method of claim 1, wherein the set of input ligands are agonists of the target protein known to be associated with the disease.

12. A computer-implemented method of screening a database of molecules to identify leads for treating a disease, the method comprising:
presenting on at least one computer display a first user interface configured to receive ASCII structural descriptions of a set of input ligands and to receive binding affinity data for the set of input ligands for a protein target known to be associated with the disease;
receiving the ASCII structural descriptions of the set of input ligands and the binding affinity data via the first user interface;
generating, from alignment data for the ASCII structural descriptions of a set of input ligands and from the binding affinity data for the set of input ligands for a target protein, a profile comprising ASCII descriptions of one or more patches in the set of input ligands;
identifying, using a computer, a set of one or more leads for treating the disease from a database, the identifying based at least in part on the profile, wherein the database comprises ASCII structural descriptions of a plurality of molecules, the ASCII structural descriptions of the plurality of molecules comprising force field information for one or more atoms described in the ASCII structural descriptions of the plurality of molecules, the identifying comprising comparing the ASCII structural descriptions of the plurality of molecules with the ASCII structural descriptions of the one or more patches, the ASCII structural descriptions of the one or more leads for treating the disease comprising the ASCII structural description of at least one of the one or more patches;
receiving a list of the set of one or more leads for treating the disease from the computer;
displaying a second user interface on the at least one computer display; and
displaying the list of the set of one or more leads for treating the disease in the second user interface.

13. The computer-implemented method of claim 12, further comprising displaying a third user interface configured to provide information about at least one of the set of input ligands or at least one of the set of one or more leads for treating the disease.

14. The computer-implemented method of claim 13, wherein at least one of the first user interface or the second user interface comprises a hyperlink configured to cause the information about at least one of the set of input ligands or at least one of the set of one or more leads for treating the disease to be displayed in the third user interface.

15. The computer-implemented method of claim 12, further comprising displaying a third user interface configured to display a graphic depiction of at least one of the one or more leads for treating the disease.

16. The computer-implemented method of claim 12, further comprising displaying a third user interface configured to receive user inputs for generating a weighting matrix for use by the computer.

17. The computer-implemented method of claim 12, further comprising displaying a third user interface configured to receive a graphical description of one or more chemical compounds.

18. A method of screening a database of chemical compounds to identify leads for treating a disease, the method comprising:
receiving, using a computer, ASCII structural descriptions of a set of input ligands and binding affinity data for the input ligands for a protein target known to be associated with the disease;

determining, using the computer and from alignment data for the ASCII structural descriptions and from the binding affinity data, a profile comprising ASCII structural descriptions of one or more patches in the set of input ligands;

storing the profile in one or more computer-readable media; and identifying one or more leads for treating the disease from a database comprising ASCII structural descriptions of a plurality of chemical compounds, the identifying comprising comparing the ASCII structural descriptions of the plurality of chemical compounds with the ASCII structural descriptions of the one or more patches, the ASCII structural descriptions of the identified one or more leads for treating the disease comprising the ASCII structural description of at least one of the one or more patches.

19. The method of claim 18, wherein determining a profile comprises:

performing one or more pairwise sequence alignments of the ASCII structural descriptions of the input ligands to determine the alignment data; and identifying the one or more patches in the input ligands based on the alignment data.

20. The method of claim 19, wherein determining a profile further comprises assigning a score to at least one of the identified one or more patches based on a length of an ASCII structural description describing at least one of the identified one or more patches.

21. The method of claim 18, wherein determining a profile further comprises assigning a score to at least one of the one or more patches based on a profile describing common factors among a set of ligands having a given binding affinity for the protein target.

22. The method of claim 18, wherein determining a profile further comprises assigning a score to at least one of the one or more patches based on a weight matrix, wherein the weight matrix describes a probability that a given position in a ligand structure is occupied by a given atom.

23. The method of claim 22, further comprising:

identifying atoms occupying a given position in each of the input ligands;

determining the probability that a first atom at the given position can be replaced with a second atom based on a frequency at which the second atom occurs at the given position in the set of input ligands; and generating the weight matrix based on the determined probabilities;

wherein assigning a score to at least one of the one or more patches comprises comparing the at least one of the one or more patches to the weight matrix, the score being based on a similarity between the weight matrix and the at least one of the one or more patches.

24. A system for screening chemical compounds, the system comprising:

a computer, the computer comprising, a database comprising ASCII structural descriptions of a plurality of chemical compounds for screening, an input component for receiving aligned ASCII structural descriptions of one or more input ligands, the one or more input ligands comprising one or more patches, and a chemical identifier component configured to identify one or more output chemical compounds from the database based on the one or more patches of the one or more input ligands by identifying chemical compounds having ASCII structural descriptions comprising at least one ASCII structural description of the one or more patches.

25. The system of claim 24, wherein the one or more patches of the one or more ligands are described in one or more consensus profiles.

26. One or more computer-readable storage media having encoded therein instructions which, when executed by a computer, cause the computer to perform a method of identifying leads for treating a disease, the method comprising:

displaying, on one or more hardware displays, a first graphical user interface (GUI) component configured to receive ASCII structural descriptions of a set of input ligands and values indicating affinities of members of the set of input ligands to bind to a target molecule known to be associated with the disease; and displaying, on the one or more hardware displays, a second GUI component configured to display descriptions of one or more leads for treating the disease identified from a database of annotated molecular ASCII structural descriptions, the one or more leads for treating the disease having been identified based on comparing the annotated molecular ASCII structural descriptions with ASCII structural descriptions of one or more patches of the set of input ligands, the ASCII structural descriptions of the one or more leads for treating the disease comprising the ASCII structural description of at least one of the one or more patches and the values indicating affinities.

* * * * *